United States Patent [19]

Anderson et al.

[11] Patent Number: 5,405,771

[45] Date of Patent: * Apr. 11, 1995

[54] TISSUE PLASMINOGEN ACTIVATOR HAVING ZYMOGENIC OR FIBRIN SPECIFIC PROPERTIES

[75] Inventors: Stephen Anderson, Princeton, N.J.; William F. Bennett, San Mateo, Calif.; David Botstein, Belmont, Calif.; Deborah L. Higgins, San Mateo, Calif.; Nicholas F. Paoni, Moraga, Calif.; Mark J. Zoller, San Francisco, Calif.

[73] Assignee: Genentech, Inc., South San Francisco, Calif.

[*] Notice: The portion of the term of this patent subsequent to Apr. 28, 2009 has been disclaimed.

[21] Appl. No.: 178,945

[22] Filed: Jan. 7, 1994

Related U.S. Application Data

[63] Continuation of Ser. No. 88,451, Jul. 6, 1993, which is a continuation of Ser. No. 770,510, Oct. 3, 1991, Pat. No. 5,262,170, which is a continuation of Ser. No. 384,608, Jul. 24, 1989, Pat. No. 5,108,901, which is a continuation-in-part of Ser. No. 240,856, Sep. 2, 1988, abandoned.

[51] Int. Cl.$^6$ .............................................. C12N 15/58
[52] U.S. Cl. ................................ 435/240.2; 435/226; 435/252.3; 435/252.33; 435/320.1
[58] Field of Search .................. 435/226, 320.1, 240.2, 435/252.33, 252.3

[56] References Cited

U.S. PATENT DOCUMENTS

| | | | |
|---|---|---|---|
| 4,753,879 | 6/1988 | Rosa et al. | 435/172.3 |
| 4,766,075 | 8/1988 | Goeddel et al. | 435/240.2 |
| 5,108,901 | 4/1992 | Anderson et al. | 435/23 |
| 5,246,850 | 9/1993 | Bennett et al. | 435/240.2 |
| 5,262,170 | 11/1993 | Anderson | 424/94.64 |
| 5,270,198 | 12/1993 | Anderson et al. | 435/240.2 |
| 5,304,482 | 4/1994 | Sambrook et al. | 435/226 |

FOREIGN PATENT DOCUMENTS

| | | |
|---|---|---|
| 0112122 | 6/1984 | European Pat. Off. |
| 0199574 | 10/1986 | European Pat. Off. |
| 0201153 | 11/1986 | European Pat. Off. |
| 0227462 | 1/1987 | European Pat. Off. |
| 0225286 | 6/1987 | European Pat. Off. |
| 0233013 | 8/1987 | European Pat. Off. |
| 0241209 | 10/1987 | European Pat. Off. |
| 0253582 | 1/1988 | European Pat. Off. |
| 0293934 | 7/1988 | European Pat. Off. |
| 0293936 | 7/1988 | European Pat. Off. |
| 0290118 | 8/1988 | European Pat. Off. |
| 0292009 | 11/1988 | European Pat. Off. |
| 0297066 | 12/1988 | European Pat. Off. |
| 0299706 | 1/1989 | European Pat. Off. |
| 0351246 | 1/1990 | European Pat. Off. |

(List continued on next page.)

OTHER PUBLICATIONS

Gardell et al., "Isolation, Characterization, and cDNA Cloning of a Vampire Bat Salivary Plasminogen Activator," *J. Biol. Chem.* 264(30): 17947–17952 (1989).

Huber and Bode, "Structural Basis of the Activation and Action of Trypsin," *Accounts of Chemical Research* 11: 114–122 (1978).

(List continued on next page.)

*Primary Examiner*—Garnette D. Draper
*Assistant Examiner*—Marianne Porta Allen
*Attorney, Agent, or Firm*—Ginger R. Dreger

[57] ABSTRACT

Tissue plasminogen activator (t-PA) zymogens and variants are prepared, including a fibrinolytically active variant of t-PA that has an amino acid alteration at a site within the protease domain of t-PA as compared with the corresponding wild-type t-PA, which alteration renders the variant zymogenic in the presence of plasmin-degraded fibrinogen, and/or fibrin (or plasma clot) specific, as compared to the corresponding wild-type t-PA. DNA sequences can be prepared that encode the zymogens and variants, as well as expression vectors incorporating the DNA sequences, and host cells transformed with the expression vectors. The zymogens and variants may be used in a pharmaceutical preparation to treat a vascular disease or condition or to prevent fibrin deposition or adhesion formation or reformation in mammals.

4 Claims, 11 Drawing Sheets

U.S. PATENT DOCUMENTS

WO84/01960  5/1984  WIPO.
WO86/01538  3/1986  WIPO.
WO87/04722  8/1987  WIPO.
WO88/05081  7/1988  WIPO.
WO88/10119  12/1988  WIPO.
WO89/00191  1/1989  WIPO.
WO90/10649  9/1990  WIPO.

OTHER PUBLICATIONS

Kassell, B. et al., "Zymogens of Proteolytic Enzymes," *Science* 180: 1022–1027 (1973).

Kaufman et al., "Expression and Amplification of DNA Introduced into Mammalan Cells," *Gene Amplification* pp. 245–250 (Cold Spring Harbor Laboratory, 1982).

Madison et al., "Serpin-Resistant Mutants of Human Tissue-Type Plasminogen Activator," *Nature* 339: 721–724 (1989).

Madison et al., "Amino Acid Residues that Affect Interaction of Tissue-Type Plasminogen Activator with Plasminogen Activator Inhibitor 1," *PNAS* 87: 3530–33 (1990).

Ny et al., "Cloning and Characterization of a cDNA for Rat Tissue-Type Plasminogen Activator," *DNA* 7(10): 671–677 (1988).

Pannekoek et al., "Mutants of Human Tissue-Type Plasminogen Activator (t-PA): Structural Aspects and Functional Properties," *Fibrinolysis* 2: 123–132 (1988).

Petersen et al., "The Effect of Polymerized Fibrin on the Catalytic Activities of One–Chain Tissue-type Plasminogen Activator as Revealed by an Analogue Resistant to Plasmn Cleavage," *Biochemica et biophysica Acta* 952: 245–254 (1988).

Pharmacia Fine Chemical Catalogue 84: 1 and 6 (1984).

Rickles et al., "Molecular Cloning of Complementary DNA to Mouse Tissue Plasminogen Activator mRNA and Its Expression during F9 Teratocarcinoma Cell Differentiation," *J. Biol. Chem.* 263(3): 1563–1569 (1988).

Rijken et al., "Fibrinolytic Properties of One-chain and Two-chain Human Extrinsic (Tissue-Type) Plasminogen Activator," *J. Biol. chem.* 257: 2920–2925 (1982).

Ringe, D., "The Sheep in Wolf's Clothing," *Nature* 339: 658–659 (1989).

Ross et al., "Plasminogen Activators," *Annual Reports in Medicinal Chemistry* 23: 111–129 (1988) Academic Press, Richard C. Allen, ed.

Tate et al., "Functional Role of Proteolytic Cleavage at Arginine-275 of Human Tissue Plasminogen Activator As Assessed by Site-Directed Mutagenesis," *Biochemistry* 26: 338–343 (1987).

TISSUE PLASMINOGEN ACTIVATOR HAVING ZYMOGENIC OR FIBRIN SPECIFIC PROPERTIES

This is a continuation of application Ser. No. 08/088,451 filed on 06 Jul. 1993, which is a continuation of application Ser. No. 07/770,510 filed 03 Oct. 1991, now U.S. Pat. No. 5,262,170 which is a continuation of application Ser. No. 07/384,608 filed 24 Jul. 1989, now U.S. Pat. No. 5,108,901, which in turn, is a continuation-in-part of Ser. No. 07/240,856 filed 02 Sep. 1988, now abandoned.

BACKGROUND OF THE INVENTION

1. Field of the Invention

The present invention is directed to particular tissue plasminogen activator (t-PA) zymogens, to methods for preparing such zymogens, and to methods and compositions utilizing such zymogens in pharmaceutical applications. In addition, the invention relates to variants having a modified structure that includes substituted amino acids within the protease domain of t-PA, which modification renders the variant zymogenic, i.e., relatively inactive in its one-chain form but active when converted to its two-chain form in the presence of fibrin, and/or more fibrin (or plasma clot) specific than wild-type (wt) t-PA.

2. Description of Background and Related Art

Plasminogen activators are enzymes that activate the zymogen plasminogen to generate the serine proteinase plasmin (by cleavage at Arg561-Val562) that degrades various proteins, including fibrin. Among the plasminogen activators studied are streptokinase, a bacterial protein, urokinase, an enzyme synthesized in the kidney and elsewhere and originally extracted from urine, and human tissue plasminogen activator (t-PA), an enzyme produced by the cells lining blood vessel walls.

The mechanism of action of each of these plasminogen activators differs: Streptokinase forms a complex with plasminogen or plasmin, generating plasminogen-activating activity, urokinase cleaves plasminogen directly, and t-PA, fibrin, and plasminogen all interact to yield maximum activity.

t-PA has been identified and described as a particularly important and potent new biological pharmaceutical agent that has shown extraordinary results in the treatment of vascular diseases, such as myocardial infarction, due in part to its high fibrin specificity and potent ability to dissolve blood clots in vivo.

Although the existence of t-PA prompted numerous investigations by several scientific groups, it was first identified as a substantially pure isolate from a natural source, and tested for requisite plasminogen activator activity in vivo, by Collen et al., U.S. Pat. No. 4,752,603 issued Jun. 21, 1988. See also Rijken et al., J. Biol. Chem., 256: 7035 (1981).

Subsequently, t-PA was fully identified and characterized by underlying DNA sequence and deduced amino acid sequence based on successful work employing recombinant DNA technology resulting in large quantities of t-PA in a distinct milieu. This work was reported by Pennica et al., Nature, 301: 214 (1983)) and in U.S. Pat. No. 4,766,075, issued 23 Aug. 1988.

Based on these disclosures, it seems now clear that the t-PA molecule contains five domains that have been defined with reference to homologous or otherwise similar structures identified in various other proteins such as trypsin, chymotrypsin, plasminogen, prothrombin, fibronectin, and epidermal growth factor (EGF). These domains have been designated, starting at the N-terminus of the amino acid sequence of t-PA, as 1) the finger region (F) that has variously been defined as including amino acids 1 to about 44, 2) the growth factor region (G) that has been variously defined as stretching from about amino acids 45 to 91 (based upon its homology with EGF), 3) kringle one (K1) that has been defined as stretching from about amino acid 92 to about amino acid 173, 4) kringle two (K2) that has been defined as stretching from about amino acid 180 to about amino acid 261, and 5) the so-called serine protease domain (P) that generally has been defined as stretching from about amino acid 264 to the C-terminal end of the molecule. These domains, which are situated generally adjacent to one another, or are separated by short "linker" regions, account for the entire amino acid sequence of from 1 to 527 amino acids of the putative mature form of t-PA.

Each domain has been described variously as contributing certain specific biologically significant properties. The finger domain has been characterized as containing a sequence of at least major importance for high binding affinity to fibrin. (This activity is thought important for the high specificity that t-PA displays with respect to clot lysis at the locus of a fibrin-rich thrombus.) The growth factor-like region likewise has been associated with cell surface binding activity. The kringle 2 region also has been strongly associated with fibrin binding and with the ability of fibrin to stimulate the activity of t-PA. The serine protease domain is responsible for the enzymatic cleavage of plasminogen to produce plasmin.

Despite the profound advantages associated with natural t-PA as a clot-dissolving agent, it is not believed that the natural protein necessarily represents the optimal t-PA agent under all circumstances. Therefore, several variants have been proposed or devised to enhance specific properties of t-PA. Certain of those variants address disadvantages associated with the use of natural t-PA in situations where an agent with a longer half-life or slower clearance rate would be preferred, e.g., in the treatment of deep-vein thrombosis and following reperfusion of an infarct victim, or where a single-chain agent is preferred.

For example, removal of a substantial portion or all of the finger domain results in a molecule with substantially diminished fibrin binding characteristics, albeit in return there is a decrease in the overall rate of clearance of the resultant entity—See WO 89/00197 published 12 Jan. 1989.

Variants are described in EPO Pat. Publ. No. 199,574 that have amino acid substitutions at the proteolytic cleavage sites at positions 275, 276, and 277. These variants, characterized preferentially as t-PA variants having an amino acid other than arginine at position 275, are referred to as protease-resistant one-chain t-PA variants in that, unlike natural t-PA, which can exist in either a one-chain or two-chain form, they are resistant to protease cleavage at position 275 and are therefore not converted metabolically in vivo into a two-chain form. This form is thought to have certain advantages biologically and commercially, in that it is more stable while the fibrin binding and fibrin stimulation are increased relative to two-chain t-PA. Furthermore, plasminogen activators are described that comprise one domain capable of interacting with fibrin and the protease domain of urokinase, with one embodiment being urokinase altered to make it less susceptible to forming two-chain urokinase. See WO 88/05081 published 14 Jul. 1988.

For further patent literature regarding modification of the protease cleavage site of t-PA, see, for example, EPO Pat. Nos. 241,209; EP 201,153 published Nov. 12, 1986; EP 233,013 published Aug. 19, 1987; EP 292,009 published Nov. 23, 1988; EP 293,936 published Dec. 7, 1988; and EP 293,934 published Dec. 7, 1988; and WO 88/10119.

Glycosylation mutants at 117–119, 184–186, and 448–450 exhibited higher specific activity as the mole percent carbohydrate was reduced. See EPO Pub. No. 227,462 published Jul. 1, 1987. This patent application additionally discloses using an assay of fibrin/fibrin degradation products and teaches that one may also modify the t-PA molecule at positions 272–280 or delete up to 25 amino acids from the C-terminus. Further, the t-PA mutants with Asn119, Ala186 and Asn450, which have the N-glycosylation sites selectively removed by DNA modification but contain residual O-linked carbohydrate, were found to be about two-fold as potent as melanoma t-PA in an in vitro lysis assay. See EPO Publ. No. 225,286 published Jun. 10, 1987.

Replacement of the amino acid at 449 of t-PA with any amino acid except arginine to modify the glycosylation site, as well as modification of Arg275 or deletion of the −3 to 91 region, is also taught. See WO 87/04722 published Aug. 13, 1987. An amino acid substitution at position 448 of t-PA is disclosed as desirable to remove glycosylation. See EPO Pub. No. 297,066 published Dec. 28, 1988. The combination of modifications at positions 448–450 and deletion of the N-terminal 1–82 amino acids is disclosed by WO 89/00191 published Jan. 12, 1989. Additionally, urokinase has been modified in the region of Asp302-Ser303-Thr304 to prevent glycosylation. See EPO Pub. No. 299,706 published 18 Jan. 1989.

However, alteration of the glycosylation sites, and in particular that at amino acid 117, seems invariably to result in a molecule having affected solubility characteristics that may result additionally in an altered circulating half-life pattern and/or fibrin binding characteristics. See EPO Pat. Publ. No. 238,304, published 23 Sep. 1987.

When the growth factor domain of t-PA is deleted, the resultant variant is still active and binds to fibrin, as reported by A. J. van Zonneveld et al., Thrombos. Haemostas., 54 (1) 4 (1985). Various deletions in the growth factor domain have also been reported in the patent literature. See EPO Publ. No. 241,209 (des-51-87), EPO Publ. No. 241,208 (des-51-87 and des-51-173), PCT 87/04722 (deletion of all or part of the N-terminal 1–91), EPO Publ. No. 231,624 (all of growth factor domain deleted), and EPO Publ. No. 242,836 and Jap. Pat. Appl. Kokai No. 62-269688 (some or all of the growth factor domain deleted).

It has further been shown that t-PA can be modified both in the region of the first kringle domain and in the growth factor domain, resulting in increased circulatory half-life. See EPO Pat. Publ. No. 241,208 published Oct. 14, 1987. The region between amino acids 51 and 87, inclusive, can be deleted from t-PA to result in a variant having slower clearance from plasma. Browne et al., J. Biol. Chem., 263: 1599–1602 (1988). Also, t-PA can be modified, without adverse biological effects, in the region of amino acids 67 to 69 of the mature, native t-PA, by deletion of certain amino acid residues or replacement of one or more amino acids with different amino acids. See EPO Pat. Publ. No. 240,334 published Oct. 7, 1987.

A hybrid of t-PA/urokinase using the region of t-PA encompassing amino acids 273–527 is also disclosed. See EPO 290,118 published Nov. 9, 1988.

Serpin-resistant mutants of human t-PA with alterations in the protease domain, including d296–302 t-PA, R304S t-PA, and R304E t-PA, are disclosed in Madison et al., Nature, 339: 721–724 (1989); see also the accompanying article by Dagmar Ringe in the same issue.

A general review of plasminogen activators and second-generation derivatives thereof can be found in Harris, Protein Engineering, 1: 449–458 (1987). Other reviews of t-PA variants include Pannekoek et al., Fibrinolysis, 2: 123–132 (1988) and Ross et al., in Annual Reports in Medicinal Chemistry, Vol. 23, Chapter 12 (1988).

While the foregoing disclosures provide evidence that newer and, in various respects, better t-PA agents are at hand, there are currently no t-PA molecules described that only become activated when they reach the site of the clot to be dissolved. Currently, the t-PA molecules are active in the presence of fibrin and/or plasma proteins or whole blood, whether they are in the one-chain or two-chain form. It would be desirable to have a zymogenic t-PA that in the presence of fibrin requires clipping of its one-chain form to its two-chain form to become fully active. Such variant molecules would likely exhibit fewer side effects, such as less bleeding, and have fibrinogen sparing properties, thereby providing medical science important new alternatives in the treatment of cardiovascular disease and numerous other medical conditions that arise from thromboembolic occlusion of blood vessels, as well as in the prevention of the formation of adhesions.

It would also be desirable to provide a t-PA molecule that, relative to wild-type t-PA, has a higher fibrin-stimulated (or a plasma clot-stimulated) activity than fibrinogen-stimulated (or plasma-stimulated) activity, i.e., is fibrin (or plasma clot) specific, so that it will act only at the site of the clot and not systemically.

Accordingly, it is an object of this invention to provide zymogenic and/or fibrin-specific t-PA molecules that exhibit improved therapeutic and pharmaceutical characteristics.

It is another object to provide for the treatment of conditions that admit the use of clot-dissolving agents that are active only at the site of the clot and are useful at higher levels than other such agents.

These and other objects will be apparent to one of ordinary skill in the art.

SUMMARY OF THE INVENTION

These objects are achieved by the provision of a tissue plasminogen activator (t-PA) zymogen capable of converting to the enzymatically active form of t-PA upon cleavage by plasmin. In another aspect, the invention provides a t-PA variant having an amino acid alteration at a site or sites within the protease domain of t-PA as compared with the corresponding wild-type t-PA, which alteration renders the variant zymogenic as compared to the corresponding wild-type t-PA.

In one particularly preferred embodiment, the t-PA is human t-PA and the alteration is in the region of 305, inclusive, such as a substitution of histidine for phenylalanine at position 305 of the corresponding wild-type t-PA.

In other embodiments, this invention relates to a DNA sequence encoding the zymogen and variant described above, replicable expression vectors capable of expressing the DNA sequence in a transformant host cell, and microorganisms and cell cultures transformed with the vector.

In still another embodiment, the invention provides a method comprising:

(a) introducing an amino acid variation into the protease domain of t-PA; and (b) screening the resultant t-PA variant for zymogenic character.

In other aspects, the invention supplies a human tissue plasminogen activator (t-PA) variant capable of exhibiting one or more of the following biological activities: zymogenic activity, fibrin specificity, or plasma clot specificity, characterized in that it contains an amino acid alteration in its protease domain as compared with the corresponding wild-type t-PA, which alteration is responsible for said biological activity, provided that such alteration excludes alterations solely in the regions of 270–280, 448–450, and 502–527. Preferably, the variant is such that the alteration is a substitution.

In another aspect, the invention provides a method comprising:

(a) introducing an amino acid variation into the protease domain of tissue plasminogen activator (t-PA); and (b) screening the resultant t-PA variant for its capability of exhibiting one or more of the following biological activities: zymogenic activity, fibrin specificity, or plasma clot specificity.

In further embodiments the invention provides DNA sequences and replicable vectors encoding the above-described variants and host cells transformed with them.

In yet another embodiment, the invention is directed to a composition for treating a vascular condition or disease comprising a therapeutically effective amount of the zymogen or variant herein in admixture with a pharmaceutically acceptable carrier. Also encompassed herein is a composition for preventing fibrin deposition or adhesion formation or reformation comprising a therapeutically effective amount of the zymogen or variant herein in admixture with a pharmaceutically acceptable carrier.

In still another embodiment, the invention provides a method of treating a vascular condition or disease in a mammal comprising administering an effective amount of the appropriate composition described above to the mammal.

The invention also provides a method of treating a mammal to prevent fibrin deposition or adhesion formation or reformation comprising administering to a site on the mammal of potential fibrin or adhesion formation an effective amount of the appropriate composition described above.

The first aspect of the present invention is based, inter alia, upon specific successful research demonstrating that certain t-PA molecules are zymogens in the presence of a stimulator of t-PA activity, such as plasmin-degraded fibrinogen fragments, and thus can have their fibrinolytic activity turned off when generally in the plasma and activated when proximate to plasmin at the site of the clot. Thus, the zymogen is activated on demand for specific localized clot therapy. The zymogens herein are expected to be fibrinogen sparing and are generally useful in higher doses than their non-zymogenic counterparts, resulting in faster clot lysis and lysis of more clots.

The second aspect of this invention is to obtain a t-PA molecule that is more fibrin (or plasma clot) specific so that it will act more preferentially at the site of the clot than unmodified t-PA.

DETAILED DESCRIPTION OF THE PREFERRED EMBODIMENTS

A. Definitions

Figure 1:
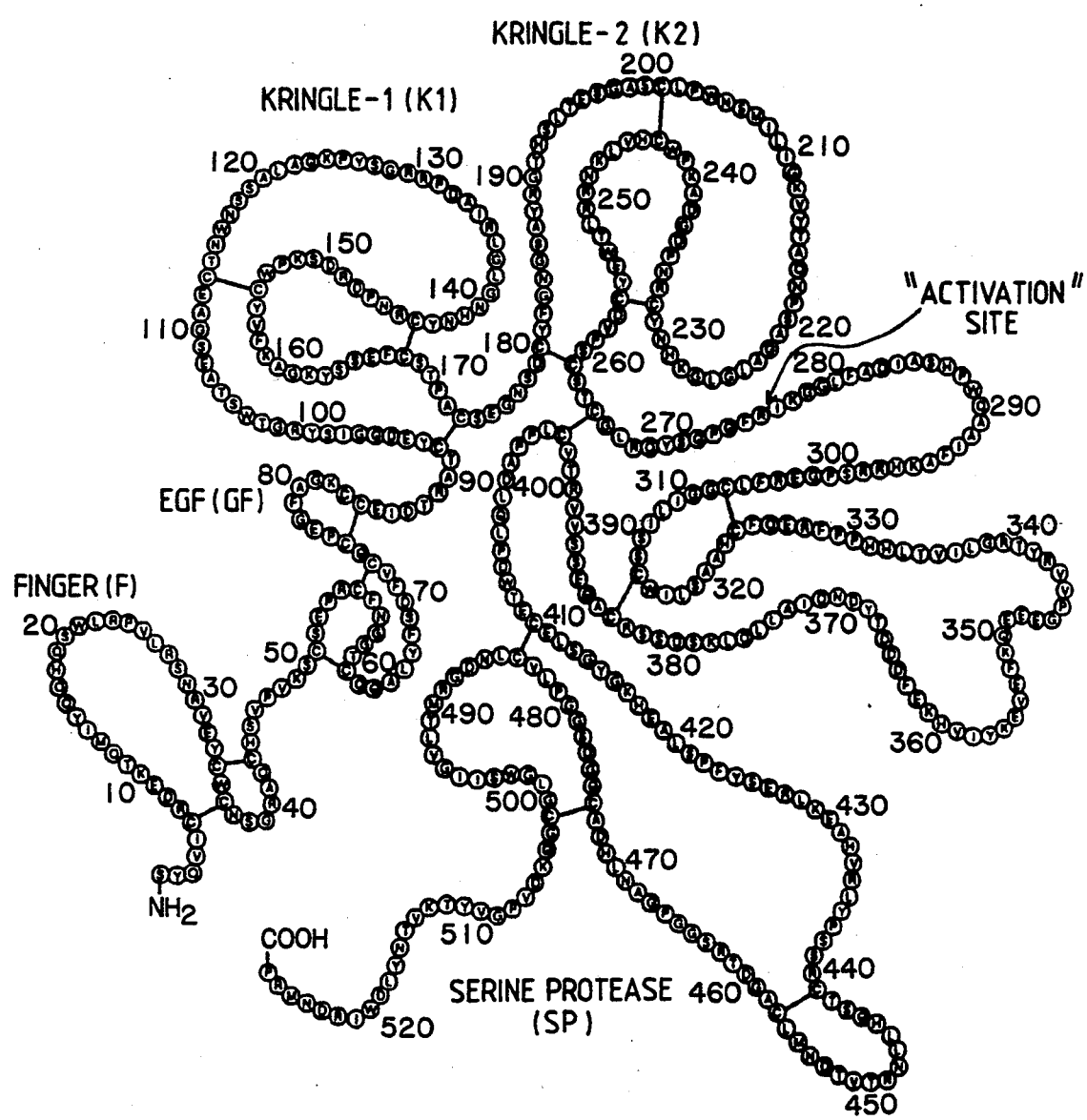
FIG. 1 depicts the primary structure of t-PA showing the location of the five domains, the disulfide bridging, and the activation site where the molecule is clipped into a two-chain molecule.

As used herein, the terms "human tissue plasminogen activator," "human t-PA," and "t-PA" denote human extrinsic (tissue-type) plasminogen activator having two functional regions consisting of a protease domain that is capable of converting plasminogen to plasmin and an N-terminal region believed to be responsible for fibrin binding. These three terms therefore include polypeptides containing these functional domains as part of the overall sequence. t-PA is suitably produced, e.g., by recombinant cell culture systems, in bioactive forms comprising the protease portion and portions of t-PA otherwise native to the source of the t-PA. It will be understood that natural allelic variations exist and occur from individual to individual, demonstrated by (an) amino acid difference(s) in the overall sequence.

As used herein, the term "wild-type t-PA" refers to the t-PA encoded by the cDNA reported by U.S. Pat. No. 4,766,075, supra, the disclosure of which is incorporated herein by reference. The t-PA thus encoded is suitably a t-PA molecule from any native source or any recombinant expression system, including 293 or 294 cells, Chinese hamster ovary cells, etc.

As used herein, the term "protease domain" refers to the region of the mature form of wild-type t-PA from amino acid 264 to amino acid 527, inclusive.

As used herein, the terms "zymogen," "zymogenic," and "zymogenic activity" used to describe the t-PA herein must meet either one or both of the definitions given below. In the first definition, these terms signify that in the presence of plasmin-degraded fibrinogen the t-PA requires clipping of its one-chain form to its two-chain ("enzymatically active") form, as occurs in the presence of plasmin, to increase its enzymatic activity, as defined below, under the conditions of the assay described below.

In the presence of fibrinogen fragments, the one-chain form of the t-PA (zymogen) as defined herein is less active, as measured by the assay described below, than wild-type two-chain t-PA and is converted to its more enzymatically active form when activated by exposure to a level of plasmin that effects complete conversion of the single-chain form to the double-chain form. In general, the activity of the one-chain form is reduced to 50% or less of the activity of the corresponding two-chain form, preferably to 20% or less, and more preferably to less than 10% of the activity; and, upon clipping to the two-chain form, the activity is increased to from about 20 to over 100%, preferably to at least 50%, of the activity of the wild-type two-chain form.

The variant is assayed for its enzymatic activity by determining the kinetics of conversion of plasminogen to plasmin using the chromogenic plasmin substrate S-2251 in the presence of fibrinogen fragments, using the assay described in Example I below.

For purposes herein regarding the first definition of a zymogen, a zymogen is one that under the above conditions exhibits a distinct lag in the plasmin production, and thus in the increase in A405, when plotted vs. time$^2$, yet exhibits linear kinetics with increasing time. A description of time$^2$ kinetics can be found in Nieuwenhuizen, W., Voskuilen, M., Traas, D., Hoegee-de Nobel, B., Verheijen, J. H., in *Fibrinogen—Structural Variants and Interactions*, eds. A. Henschen, B. Hessel, J. McDonagh, T. Saldeen (1985), p. 331–342, the disclosure of which is incorporated by reference. Without being limited to any one theory, this effect is presumably due to the plasmin-catalyzed conversion of the one-chain to two-chain form, thereby leading to activation of the t-PA zymogen. This contrasts with the observance of linear kinetics from the beginning of the assay for the wild-type one-chain t-PA, the wild-type two-chain t-PA, and the two-chain form of the zymogenic t-PA.

In the second, alternative definition, a "zymogen" specifically refers to a t-PA molecule that in an assay of enzymatic activity exhibits a larger differential activity between the one-chain form and the two-chain form than wild-type recombinant t-PA (rt-PA). The differential activity of the zymogen is preferably at least approximately 1.5 times that of wild-type rt-PA. This activity can be obtained by lowering the activity of the one-chain form to a greater extent than that of the two-chain form relative to wild-type rt-PA; raising the activity of the two-chain form to a greater extent than that of the one-chain form relative to wild-type rt-PA; or any combination of events described above that yield the described effect. The zymogenic character of wild-type t-PA is described in Loscalzo, *J. Clin. Invest.*, 82: 1391–1397 (1988) and Ranby et al., *Thrombosis Research*, 27: 175–183 (1982).

The expression "fibrin specificity" refers to the activity of a mutant that exhibits a higher ratio of fibrin-dependent specific activity to fibrinogen-dependent specific activity in a S-2251 assay (in either the one-chain or two-chain form) than wild-type rt-PA, and preferably a ratio of at least 1.5.

The expression "plasma clot specificity" refers to the activity of a mutant that exhibits a higher ratio of plasma clot-dependent specific activity to plasma-dependent specific activity in a S-2251 assay (in either the one-chain or two-chain form) than wild-type rt-PA, and preferably a ratio of at least 1.5.

As used herein, "transient expression system" denotes a cell culture containing cells transfected with a t-PA variant-encoding vector that expresses the DNA sequence encoding the variant transiently, i.e., in a manner that may not be stable. Such cells are deemed "capable of transient expression."

B. General Methods

1. Amino Acid Sequence Variants

For purposes of discussing the variants herein, reference is made to FIG. 1, which illustrates the primary structure of t-PA.

In FIG. 1, the letters in the circles are single-letter amino acid codes, the connecting lines between chains indicate disulfide bridging, the open circles indicate glycosylation sites, and the designations F, GF, K1, K2, and SP indicate, respectively, the finger, growth factor, kringle 1, kringle 2, and serine protease domains.

For purposes of shorthand designation of t-PA variants described herein, it is noted that numbers refer to the amino acid residue/position along the amino acid sequences of putative mature t-PA (EPO Publ. No. 93,619). Amino acid identification uses the single-letter alphabet of amino acids, i.e.,

| Asp | D | Aspartic acid | Ile | I | Isoleucine |
|-----|---|---------------|-----|---|------------|
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

The designation for a substitution variant herein consists of a letter followed by a number followed by a letter. The first (leftmost) letter designates the amino acid in the wild-type, mature t-PA. The number refers to the amino acid position where the amino acid substitution is being made, and the second (right-hand) letter designates the amino acid that is used to replace the wild-type amino acid. The designation for an insertion variant consists of the letter i followed by a number designating the position of the residue in wild-type, mature t-PA before which the insertion starts, followed by one or more capital letters indicating, inclusively, the insertion to be made. The designation for a deletion variant consists of the letter d followed by the number of the start position of the deletion to the number of the end position of the deletion, with the positions being based on the wild-type, mature t-PA. Multiple mutations are separated by a comma in the notation for ease of reading them.

Examples of the nomenclature are as follows: a substitution variant where the phenylalanine at position 305 of the wild-type t-PA is replaced with a histidine residue is designated F305H. A substitution variant with multiple substitutions at consecutive positions 296–299 of AAAA for KHRR is designated K296A, H297A, R298A, R299A. An insertion variant where cysteine and valine are inserted after position 305 of wild-type t-PA is designated i305CV. A deletion variant where the amino acids at positions 300 to 305 are deleted from the wild-type, mature t-PA is designated d300–305. The notation 't-PA' follows after each mutant.

One preferred class of zymogens herein are those that have a substitution, deletion, or insertion in or around position 305 of wild-type t-PA. These variants include those with an amino acid other than phenylalanine at position 305 of the corresponding wild-type t-PA. More preferably, such variants are those with an amino acid at position 305 having a side chain that can act or does act as a hydrogen bond donor, such as one containing a hydroxyl group or nitrogen atom. Still more preferably, such amino acids are arginine, lysine, tyrosine, asparagine, glutamine, and histidine, most preferably histidine. Preferred insertional zymogenic variants of this type include those with one or more, preferably one, amino acid inserted after the amino acid at position 304 or 305, such as the amino acids described above, i.e., those with a side chain that can act or acts as a hydrogen bond donor, such as one containing a hydroxyl group or nitrogen atom, e.g., arginine, lysine, tyrosine, asparagine, glutamine, and histidine, most preferably histidine. Preferred deletion zymogenic variants include those with deletions in the region of 297 to 305, inclusive, of the wild-type t-PA, including d297 t-PA, d298 t-PA, etc. and combinations thereof, such as d297–299 t-PA or d297,d305 t-PA.

Particular embodiments of the above-noted zymogen variants include: F305H t-PA; F305T t-PA; F305N t-PA; F305K t-PA; F305R t-PA; F305Q t-PA; i304H t-PA; i304T t-PA; i304N t-PA; i304K t-PA; i304R t-PA; i304Q t-PA; i304HH t-PA; i305H t-PA; i305T t-PA; i305N t-PA; i305K t-PA; i305R t-PA; i305Q t-PA; i304H, i305H t-PA; i305HH t-PA; d297 t-PA; d298 t-PA; d299 t-PA; d300 t-PA; d301 t-PA; d302 t-PA; d303 t-PA; d304 t-PA; d305 t-PA; d297–298 t-PA; d297–299 t-PA; d297–300 t-PA; d297–301 t-PA; d297–302 t-PA; d297–303 t-PA; d297–304 t-PA; d297–305 t-PA; d300–301 t-PA; d300–302 t-PA; d300–303 t-PA; d300–304 t-PA; d300–305 t-PA; d304–305 t-PA; d297,d300 t-PA; d297,d305 t-PA; d1–44,N184D,F305H t-PA; d1–44,F305H t-PA; d1–44,I210R,G211A,K212R,V213R,F305H t-PA; d1–44, I210R,G211A, K212R,V213K, F305H t-PA; d1–44 ,V213K, F305H t-PA; d1–44,T252R, F305H t-PA; d1–44,V213K, T252R, F305H t-PA; d1–44, I210K, F305H t-PA; d1–44, I210R, G211H, K212Q, V213K, F305H t-PA; I210R, G211H, K212Q, V213K, F305H t-PA; I210R,G211A,K212R,V213R,F305H t-PA; d1–44, N184D, I210R, G211A, K212R, V213R, T252R, F305H t-PA; N184D, I210R,G211A, K212R,V213R,T252R, F305H t-PA; d92–179, F305H t-PA; d92–179,I210R,G211A, K212R,V213R,F305H t-PA; d92–179,N184D, I210R,G211A, K212R,V213R,T252R, F305H t-PA; d92–179,I210R,G211A, K212R,V213R, T252R, F305H t-PA; Y67N, F305H t-PA; d1–44, Y67N, F305H t-PA; and the T252R or N184S analogues thereof or combinations thereof. (The changes other than those in the protease domain are described further below.)

Of these, the preferred zymogen variants are F305H t-PA; F305T t-PA; F305N t-PA; F305K t-PA; F305R t-PA; F305Q t-PA; i304H t-PA; d1–44, F305H t-PA; d92–179, F305H t-PA; d1–44 ,N184D, F305H t-PA; d1–44, I210R,G211A, K212R,V213R, F305H t-PA; d1–44,I210R,G211A,K212R,V213K,F305H t-PA; I210R,G211A,K212R,V213R,F305H t-PA; d92–179, I210R, G211A, K212R, V213R, F305H t-PA; d92–179, N184D, I210R, G211A, K212R, V213R, F305H t-PA; d92–179, N184D, I210R, G211A, K212R,V213R, T252R, F305H t-PA; d1–44, N184D, I210R, G211A, K212R, V213R, T252R, F305H t-PA; and N184D, I210R, G211A, K212R, V213R, T252R, F305H t-PA.

More preferred variants of the first class of zymogens are F305H t-PA; F305T t-PA; F305N t-PA; F305Q t-PA; i304H t-PA; d1–44,F305H t-PA; d92–179,F305H t-PA, and the most preferred F305H t-PA.

Another preferred class of zymogens herein, as well as a class of variants that may alternatively or additionally be fibrin (or plasma clot) specific, are variants with one or more alterations in small regions of the protease domain identified as having charged amino acid side chains, which regions and/or regions adjacent thereto may be responsible for the interaction of t-PA with other substances that might affect its various activities.

The regions identified for testing for activity by this method are at residue numbers 267, 283–287, 296–299,3- 03–304, 322, 326–327, 331–332, 339–342, 347–351, 353–356, 360–362, 364–366, 369–371, 378–383, 387–392, 400–405, 408, 410, 416–418, 426–430, 432–434, 440, 445–449, 449–453, 460–462, 471–472, 477, 487–489, 505–506, 513, 519–523, and 523–526 of the corresponding wild-type t-PA.

One or more of these regions, or subunits thereof, are altered to determine if the desired biological property or properties will be obtained. The charged residues (Arg, Asp, His, Lys, and Glu) are suitably identified using a technique known as alanine-scanning mutagenesis, disclosed in Cunningham and Wells, *Science*, 244: 1081–1085 (1989), the disclosure of which is incorporated herein by reference, and replaced with a neutral or negatively charged amino acid to affect the interaction of the amino acids with the surrounding aqueous environment in or outside the cell.

The mutants found to be in this second preferred class of zymogens and fibrin-specific molecules are those wherein the amino acids replaced are at position(s) 267, 283+287, 296–299, 303–304, 331–332, 339+342, 347–349+351, 364–366, 408, 410, 416–418, 426–427+4- 29–430, 432–434, 440, 445+449, 449+453, 460+462, and/or 477 of the corresponding wild-type t-PA, where the "+" indicates replacements only at the positions designated, and the "-" indicates replacements at all positions designated.

For the alanine scanning mutagenesis, it is preferable that an amino acid be substituted that will neutralize the charge of the corresponding amino acid of the wild-type t-PA, rather than confer an opposite charge on the molecule. Any hydrophobic, essentially uncharged or oppositely charged amino acid can be used, including, as preferred, alanine, glycine, serine, threonine, asparagine, glutamine, valine, leucine, isoleucine, phenylalanine, or tyrosine. Among these, small amino acids, such as alanine, serine and threonine, are preferred over larger amino acids such as valine, leucine, and isoleucine. Charged amino acids such as aspartic acid or glutamic acid are less preferred.

More preferably, the amino acid used for replacement is either alanine, serine, threonine, asparagine, glutamine, phenylalanine, or tyrosine, and more preferably still, alanine, serine, or threonine. Alanine is the most preferred amino acid for this purpose because it eliminates the side-chain beyond the beta-carbon and is less likely to alter the main-chain conformation of the wild-type t-PA molecule. Further, alanine is frequently found in both buried and exposed positions (Creighton, T. E., in *The Proteins* (eds. W. H. Freeman & Co., N.Y.); Chothia, C. (1976) *J. Mol. Biol.*, 150:1).

Preferred variants of this latter class of zymogens or fibrin (or plasma clot) specific variants are those that are inclusive of modifications within the protease domain of t-PA with the exception of the variants D365A t-PA, R462L t-PA, A473S t-PA, d296–304 t-PA, d296–302 t-PA, R298E t-PA, R299E t-PA, R304E t-PA, R304S t-PA, d296–299 t-PA, and K296E,R298E,R299E t-PA.

More specifically, they are those that have one or more substitutions at position(s) 267, 283, 287, 296, 297, 298, 299, 303, 304, 331, 332, 339, 342, 347, 348, 349, 351, 364, 365, 366, 408, 410, 416, 417, 418, 426, 427, 429, 430, 432, 434, 440, 445, 449, 453, 460, 462, or 477, or combinations thereof, of the corresponding wild-type t-PA.

More preferably, the protease domain variants have substitutions at position(s) 267, 283+287, 296–299, 303–304, 331–332, 339+342, 347–349+351, 364–366, 408, 410, 416–418, 426–427+429–430, 432+434, 440, 445+449, 449+453, 460+462, and 477 of the corresponding wild-type t-PA, where the "+" indicates alterations only at the positions designated, not positions in between, and the "–" indicates alterations at all positions designated, including those in between.

Still more preferably, the protease domain variants of the latter class of zymogens or fibrin (or plasma clot) specific variants are R267A t-PA, D283A, H287A t-PA, K296A, H297A, R298A, R299A t-PA, E303A, R304A t-PA, H331A, H332A t-PA, R339A, R342A t-PA, E347A, E348A, E349A, K351A t-PA, D364A,D365A, D366A t-PA, E408A t-PA, E410A t-PA, K416A, H417A, E418A t-PA, E426A, R427A, K429A, E430A t-PA, H432A, R434A t-PA, R440A t-PA, H445A, R449A t-PA, R449A, D453A t PA, D460A, R462A t-PA, and D477A t-PA.

Of these, the most preferred substitution is an alanine residue in place of each of the existing residues at 296–299 of wild-type t-PA, i.e., K296A, H297A, R298A, R299A t-PA.

The preferred insertional variants that may exhibit zymogenic or fibrin-specific activity are those wherein one or more amino acids are inserted after the amino acids at positions 296, 297, 298, and/or 299. Also preferred for this purpose are those protease domain variants with an insertion consisting of either tyrosine, asparagine, lysine, arginine, or glutamine.

Other variants with one or more amino acid alterations (deletions, substitutions, or insertions, but preferably substitutions) within the protease domain (amino acids 264–527) of the native t-PA molecule are identifiable that exhibit zymogenic properties as compared to the wild-type t-PA, using one or more of the screening tests provided below.

The t-PA variants herein, in addition to being altered from the native sequence at one or more protease domain sites so as to display zymogenic and/or fibrin (or plasma clot) specific properties, also optionally contain substitutions, deletions, or insertions of residues in other regions of the native sequence to improve certain properties of the molecule, provided that changes are not made that prevent the cleavage of the one-chain form of t-PA to its two-chain form or otherwise alter a desirable biological property conferred on the molecule by the alteration(s) in the protease domain of the present invention. The preferred alterations in these other domains are provided above in the lists of the most preferred zymogen variants of the first type.

For example, the variants herein are suitably devoid of at least a portion of the finger domain, the growth factor domain, and/or the kringle 1 domain, and/or devoid of glycosylation potential at the glycosylation site surrounding amino acid 184, and suitably contain amino acid modifications in the putative lysine binding site of kringle 1 or 2.

In addition, fibrin binding of t-PA can be modulated, most preferably restored or increased, by appropriate substitutions of positively or negatively charged amino acid residues on the opposite edges of the putative ligand binding pocket of the kringle 2 domain of t-PA. The variants herein are generally prepared by site-directed mutagenesis or by excision/ligation techniques described further hereinbelow.

Specific examples of such variants include a molecule devoid of amino acids 1 to 44 (designated d1–44) and a molecule having aspartic acid at position 184 (designated N184D). Variants devoid of amino acids 1 to 44 are described more fully in WO 89/00197, supra.

All of the above variants are optionally modified in various other regions of the molecule, if such modifications still satisfy the criteria expressed herein for zymogenic and/or fibrin (or plasma clot) specific characteristics. Such modifications include, for example:

1. Kringle 1 modifications, for example, deletion of about 92 to 179, and/or
2. Kringle 2 modifications, for example, deletion of about 174–261 or modification in the region of amino acids about 205–215, especially 210–213, and/or
3. Amino acids about 244–255, especially 252 or its site, and/or
4. Amino acids about 233–242, especially 236–238, and/or
5. Known glycosylation sites such as amino acid 184, and/or
6. Glycosylation within the growth factor domain, as described in U.S. appln. Ser. No. 07/196,909 filed May 20, 1988, now abandoned, the disclosure of which is incorporated herein by reference. Briefly, the t-PA molecule is N- or O-linked glycosylated within its growth factor domain, preferably at position 67–69, where the tyrosine at position 67 is replaced with an asparagine residue, to alter the half-life of the t-PA molecule.

Many of these modifications may significantly alter clearance rates and fibrin binding relative to native t-PA. The practitioner skilled in the art will be able to determine by the appropriate assay what the optimum properties of each variant are that are desired in any particular instance.

The modification to change or insert the appropriate amino acid(s) in the native molecule to effect the above sequence variations is accomplished by any means known in the art, such as, e.g., site-directed mutagenesis or ligation of the appropriate sequence into the DNA encoding the relevant protein, as described below.

2. Site-Specific Mutagenesis

Preparation of t-PA variants in accordance herewith is preferably achieved by site-specific mutagenesis of DNA that encodes an earlier prepared variant or a nonvariant version of the protein. Site-specific mutagenesis allows the production of t-PA variants through the use of specific oligonucleotide sequences that encode the DNA sequence of the desired mutation, as well as a sufficient number of adjacent nucleotides to provide a primer sequence of sufficient size and sequence complexity to form a stable duplex on both sides of the junction being traversed. Typically, a primer of about 20 to 25 nucleotides in length is preferred, with about 5 to 10 residues on both sides of the junction of the sequence being altered. In general, the technique of site-specific mutagenesis is well known in the art as exemplified by publications such as Adelman et al., DNA, 2: 183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., Third Cleveland Symposium on Macromolecules and Recombinant DNA, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., Meth. Enzymol., 153: 3 (1987)) may be employed to obtain single-stranded DNA.

In general, site-directed mutagenesis in accordance herewith is performed by first obtaining a single-stranded vector that includes within its sequence a DNA sequence that encodes the relevant t-PA. An oligonucleotide primer bearing the desired mutated sequence is prepared, generally synthetically, for example, by the method of Crea et al., Proc. Natl. Acad. Sci. (USA), 75: 5765 (1978). This primer is then annealed with the single-stranded t-PA sequence-containing vector, and subjected to DNA-polymerizing enzymes such as E. coli polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected, via hybridization to a radioactive probe consisting of the $^{32}$P-labeled mutagenesis primer, that include recombinant vectors bearing the mutated sequence arrangement.

After such a clone is selected, the mutated t-PA region may be removed and placed in an appropriate vector for t-PA production, generally an expression vector of the type that typically is employed for transformation of an appropriate eukaryotic host. In the context of the present invention, Chinese hamster ovary (CHO) cells or 293 (human kidney cells described by Graham et al., J. Gen. Virol., 36: 59 (1977)) are preferred for the preparation of long-term stable t-PA producers. However, the invention is not limited to CHO production, as it is known that numerous other cell types are suitably employed, particularly where one desires only transient production of the enzyme for test purposes. For example, described below is a transient system employing 293 cells that provides a convenient system for production of t-PA variants for analytical purposes.

3. Cleavage/Ligation Technique

Another method for making mutations in the DNA sequence encoding the t-PA involves cleaving the DNA encoding the t-PA at the appropriate position by digestion with restriction enzymes, recovering the properly cleaved DNA, synthesizing an oligonucleotide encoding the desired amino acid and flanking regions such as polylinkers with blunt ends (or, instead of using polylinkers, digesting the synthetic oligonucleotide with the restriction enzymes also used to cleave the t-PA-encoding DNA, thereby creating cohesive termini), and ligating the synthetic DNA into the remainder of the t-PA-encoding structural gene.

4. Host Cell Cultures and Vectors

Although Chinese hamster ovary (CHO) expression ultimately is preferred for t-PA production, the vectors and methods disclosed herein are suitable for use in host cells over a wide range of eukaryotic organisms.

In general, of course, prokaryotes are preferred for the initial cloning of DNA sequences and constructing the vectors useful in the invention. For example, E. coli K12 strain 294 (ATCC No. 31,446) and E. coli strain W3110 (ATCC No. 27,325) are particularly useful. Other suitable microbial strains include E. coli strains such as E. coli B, and E. coli X1776 (ATCC No. 31,537). These examples are, of course, intended to be illustrative rather than limiting.

Prokaryotes also are useful for expression. The aforementioned strains, as well as bacilli such as Bacillus subtilis, and other enterobacteriaceae such as, e.g., Salmonella typhimurium or Serratia marcesans, and various Pseudomonas species are examples of useful hosts for expression.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, E. coli is typically transformed using pBR322, a plasmid derived from an E. coli species (see, e.g., Bolivar et al., Gene, 2: 95 (1977)). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the β-lactamase (penicillinase) and lactose promoter systems (Chang et al., Nature, 375: 615 (1978); Itakura et al., Science, 198: 1056 (1977); Goeddel et al., Nature, 281: 544 (1979)) and a tryptophan (trp) promoter system (Goeddel et al., Nucl. Acids Res., 8: 4057 (1980); EPO Appl. Publ. No. 36,776), and the alkaline phosphatase systems. While these are the most commonly used, other microbial promoters have been discovered and utilized, and details concerning their nucleotide sequences have been published, enabling a skilled worker to ligate them functionally with plasmid vectors (see, e.g., Siebenlist et al., Cell, 20: 269 (1980)).

In addition to prokaryotes, eukaryotic microbes, such as yeasts, also are suitably used herein. Saccharomyces cerevisiae, or common baker's yeast, is the most commonly used among eukaryotic microorganisms, although a number of other strains are commonly available. For example, for expression in Saccharomyces, the plasmid YRp7 (Stinchcomb et al., Nature, 282: 39 (1979); Kingsman et al., Gene, 7: 141 (1979); Tschemper et al., Gene, 10: 157 (1980)) is commonly used. This plasmid already contains the trp1 gene that provides a selection marker for a mutant strain of yeast lacking the ability to grow in tryptophan, for example, ATCC No.

44,076 or PEP4-1 (Jones, *Genetics*, 85: 12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.*, 255: 2073 (1980)) or other glycolytic enzymes (Hess et al., *J. Adv. Enzyme Reg.*, 7: 149 (1968); Holland et al., *Biochemistry*, 17: 4900 (1978)), such as enolase, glyceraldehyde-3-phosphatedehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, CHO cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication (Fiers et al., *Nature*, 273: 113 (1978)). Smaller or larger SV40 fragments are also suitably used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication typically is provided either by construction of the vector to include an exogenous origin, such as may be derived from SV40 or other viral (e.g., Polyoma, Adeno, VSV, BPV) source, or by the host cell chromosomal replication mechanism. If the vector is integrated into the host cell chromosome, the latter is often sufficient.

Satisfactory amounts of human t-PA are produced by cell cultures; however, refinements, using a secondary coding sequence, serve to enhance production levels even further. The secondary coding sequence comprises dihydrofolate reductase (DHFR) that is affected by an externally controlled parameter, such as methotrexate (MTX), thus permitting control of expression by control of the MTX concentration.

In the selection of a preferred host cell for transfection by the vectors of the invention that comprise DNA sequences encoding both variant t-PA and DHFR protein, it is appropriate to consider the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the CHO cell line deficient in DHFR activity, prepared and propagated, as described by Urlaub and Chasin, *Proc. Natl. Acad. Sci.* (USA) 77: 4216 (1980).

On the other hand, if DHFR protein with low binding affinity for MTX is used as the controlling sequence, it is not necessary to use DHFR-deficient cells. Because the mutant DHFR is resistant to MTX, MTX-containing media can be used as a means of selection, provided that the host cells are themselves MTX sensitive. Most eukaryotic cells that are capable of absorbing MTX appear to be sensitive to MTX. One such useful cell line is a CHO line, CHO-K1 (ATCC No. CCL 61).

5. Typical Cloning and Expression Methodology Employable

If mammalian cells are used as host cells, transfection generally is carried out by the calcium phosphate precipitation method as described by Graham and Van der Eb, *Virology*, 52: 546 (1978). However, other methods for introducing DNA into cells such as nuclear injection, electroporation, or protoplast fusion are also suitably used.

If yeast are used as the host, transfection is generally accomplished using polyethylene glycol, as taught by Hinnen, *Proc. Natl. Acad. Sci.* U.S.A., 75: 1929–1933 (1978).

If prokaryotic cells or cells that contain substantial cell wall constructions are used, the preferred method of transfection is calcium treatment using calcium as described by Cohen et al., *Proc. Natl. Acad. Sci.* (USA) 69: 2110 (1972), or more recently electroporation.

Construction of suitable vectors containing the desired coding and control sequences employs standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 µg plasmid or DNA fragments is used with about 1 unit of enzyme in about 20 µl of buffer solution. (Appropriate buffers and substrate amounts for particular restriction enzymes are specified by the manufacturer.) Incubation times of about one hour at 37° C. are workable. After incubation, protein is removed by extraction with phenol and chloroform, and the nucleic acid is recovered from the aqueous fraction by precipitation with ethanol.

If blunt ends are required, the preparation may be treated for 15 minutes at 15° C. with 10 units of the Klenow fragment of DNA Polymerase I (Klenow), phenol-chloroform extracted, and ethanol precipitated.

Size separation of the cleaved fragments is performed using 6 percent polyacrylamide gel described by Goeddel et al.; *Nucleic Acids Res.*, 8: 4057 (1980).

For ligation, approximately equimolar amounts of the desired components, suitably end tailored to provide correct matching, are treated with about 10 units T4 DNA ligase per 0.5 μg DNA. (When cleaved vectors are used as components, it may be useful to prevent religation of the cleaved vector by pretreatment with bacterial alkaline phosphatase.)

As discussed above, t-PA variants are preferably produced by means of specific mutation. Variants useful in the practice of the present invention are formed most readily through the use of specific oligonucleotide sequences that encode the DNA sequence of the desired mutation, as well as a sufficient number of adjacent nucleotides, to provide a sequence of sufficient size and sequence complexity to form a stable duplex on both sides of the mutation being traversed.

For analysis to confirm correct sequences in plasmids constructed, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.*, 9: 309 (1981) or by the method of Maxam et al., *Methods of Enzymology*, 65: 499 (1980).

After introduction of the DNA into the mammalian cell host and selection in medium for stable transformants, amplification of DHFR-protein-coding sequences is effected by growing host cell cultures in the presence of approximately 20,000–500,000 pM concentrations of MTX, a competitive inhibitor of DHFR activity. The effective range of concentration is highly dependent, of course, upon the nature of the DHFR gene and protein and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

In order to simplify the examples certain frequently occurring methods will be referenced by shorthand phrases.

"Plasmids" are designated by a low case p followed by an alphanumeric designation. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters representing the microorganism from which each restriction enzyme originally was obtained and then a number designating the particular enzyme. In general, about 1 μg of plasmid or DNA fragment is used with about 2 units of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular Cloning* pp. 133–134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, *Nucleic Acids Res.* 9:6103–6114, and D. Goeddel et al., 1980, *Nucleic Acids Res.* 8:4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, *J. Mol. Biol.* 98: 503–517, and hybridization as described by T. Maniatis et al., 1978, *Cell* 15: 687–701.

"Transformation" means introducing DNA into an organism so that the DNA is replicable, either as an extrachromosomal element or chromosomal integrant. Unless otherwise provided, the method used herein for transformation of *E. coli* is the CaCl$_2$ method of Mandel et al., 1970, *J. Mol. Biol.* 53: 154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 mg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id., p. 90, may be used.

"Oligonucleotides" are short length single or double stranded polydeoxynucleotides that are chemically synthesized by known methods and then purified on polyacrylamide gels.

C. Pharmaceutical Compositions

The compounds of the present invention can be formulated according to known methods to prepare pharmaceutically useful compositions, whereby the t-PA product hereof is combined in admixture with a pharmaceutically acceptable carrier vehicle. Suitable carrier vehicles and their formulation, inclusive of other human proteins, e.g., human serum albumin, are described, for example, in *Remington's Pharmaceutical Sciences*, 16th ed., 1980, Mack Publishing Co., edited by Oslo et al., the disclosure of which is hereby incorporated by reference. Such compositions will typically contain an effective amount of the variant herein, for example, from about 0.5 to about 5 mg/ml, together with a suitable amount of carrier vehicle to prepare pharmaceutically acceptable compositions suitable for effective administration to the host. The t-PA variant herein may be administered parenterally to subjects suffering from cardiovascular diseases or conditions, or by other methods that ensure its delivery to the bloodstream in an effective form.

Compositions particularly well suited for the clinical administration of variant t-PA products employed in the practice of the present invention include, for example, sterile aqueous solutions, or sterile hydratable powders such as lyophilized protein. It is generally desirable to include further in the formulation an appropriate amount of a pharmaceutically acceptable salt, generally in an amount sufficient to render the formulation isotonic. A pH regulator such as arginine base, and phosphoric acid, are also typically included in sufficient quantities to maintain an appropriate pH, generally from 5.5 to 7.5. Moreover, for improvement of shelf-life or stability of aqueous formulations, it may also be desirable to include further agents such as glycerol. In this manner, variant t-PA formulations are rendered appropriate for parenteral administration, and, in particular, intravenous administration.

Dosages and desired drug concentrations of pharmaceutical compositions of the present invention may vary depending on the particular use envisioned. For example, in the treatment of deep vein thrombosis or peripheral vascular disease, "bolus" doses, on the order of about 0.05 to about 0.2 mg/kg, will typically be preferred with subsequent administrations, on the order of about 0.1 to about 0.2 mg/kg, being given to maintain an approximately constant blood level, preferably on the order of about 3 mg/ml.

However, for use in connection with emergency medical care facilities where infusion capability is generally not available and due to the generally critical nature of the underlying disease (e.g., embolism, infarct), it will generally be desirable to provide somewhat larger initial doses, such as an intravenous bolus on the order of about 0.3 mg/kg.

For example, the t-PA variant hereof is suitably administered parenterally to subjects suffering from cardiovascular diseases or conditions. Dosage and dose rate may be parallel to or higher than that currently in use in clinical investigations of other cardiovascular, thrombolytic agents, e.g., about 1–2 mg/kg body weight as an intravenous or intra-arterial dose over 1.5 to 12 hours in human patients suffering from myocardial infarction, pulmonary embolism, etc. Higher doses may be tolerated because the variants herein have lower side effects than wild-type t-PA, leading to faster and more complete clot lysis.

As one example of an appropriate dosage form, a vial containing 50 mg t-PA, arginine, phosphoric acid, and polysorbate 80 is reconstituted with 50 ml sterile water for injection and mixed with a suitable volume of 0.9 percent sodium chloride injection.

The t-PA variants herein also are useful to prevent fibrin deposition or adhesion formation or reformation. One embodiment of this use is described in U.S. Ser. No. 07/125,319 filed Nov. 25, 1987 now abandoned, the disclosure of which is incorporated herein by reference. Generally, such treatment involves topical administration of a composition to a site of potential fibrin or adhesion formation wherein the composition comprises a therapeutically effective amount of the t-PA variant in a sparingly soluble form that is continuously released at that site for a period of time of about from three days to two weeks. Typically, the t-PA variant is administered at a dosage sufficient to prevent fibrin deposition or formation of adhesions following surgery, infection, trauma, or inflammation. Typically, this amount is from 0.02 mg/g of gel to 25 mg/g of gel, with preferred amounts from 0.20 mg/g gel to about 2.5 mg/g of gel, most preferably from 0.25 mg/g to about 1.0 mg/g of gel.

The vehicle in which the t-PA is typically formulated for preventing adhesion formation is a semisolid, mucilaginous pharmaceutically inert carrier for positioning the enzyme at the site of potential adhesion formation. Such a carrier includes long-chain hydrocarbons or vegetable oils and waxes composed of mixtures of saturated and unsaturated fatty acid glycerides or mixtures of modified saturated and unsaturated fatty acid glycerides. Examples include semisolid vehicles such as petroleum jelly or semi-synthetic glycerides, polyhydroxy solvents such as glycerol, long-chain hydrocarbons, bioerodable polymers, or liposomes.

The following examples are intended merely to illustrate the best mode now known for practicing the invention, but the invention is not to be considered limited thereto.

All literature and patent application citations herein are expressly incorporated by reference.

EXAMPLE I

A. Preparation and Utilization of Expression Vector for Recombinant Production of the t-PA Variants Hereof 1. Construction of Plasmid p7-1H a) Plasmid pCISt-PA Plasmid pCISt-PA was prepared as follows. The vector pCIHt-PA containing the cytomegalovirus enhancer and promoter, the cytomegalovirus splice donor site and intron, the Ig variable region splice acceptor site, the cDNA-encoding t-PA (Pennica et al., *Nature*, 301: 214 (1983)) and the hepatitis surface antigen polyadenylation and transcription termination site was constructed first:

The vector pF8CIS containing the cytomegalovirus enhancer (Boshart et al., *Cell*, 41: 520 (1985)) and promoter (Thomsen et al., *Proc. Natl. Acad. Sci.* (U.S.A.) 81: 659 (1984)), the cytomegalovirus splice donor site and a portion of an intron (Sternberg et al., *J. of Virol.*, 49: 190 (1984)), the Ig variable region intron and splice acceptor site, the cDNA encoding factor VIII, and the SV40 polyadenylation site was constructed. The three parts of the construction are detailed below.

1. The ampicillin resistance marker and replication origin of the final vector was derived from the starting plasmid pUC13pML, a variant of the plasmid pML (Lusky et al., *Nature*, 293: 79 (1981)). pUC13pML was constructed by transferring the polylinker of pUC13 (Veira et al., *Gene*, 19: 259 (1982)) to the EcoRI and HindIII sites of pML. A second starting plasmid pUC8CMV was the source of the CMV enhancer, promoter and splice donor sequence. pUC8CMV was constructed by inserting nucleotides 1 through 732 for the CMV enhancer, promoter and splice donor sequence into the blunted PstI and SphI sites of pUC8—Veira et al., supra. Synthetic BamHI-HindIII linkers (commercially available from New England Biolabs) were ligated to the cohesive BamHI end, creating a HindIII site. Following this ligation a HindIII-HincII digest was performed. This digest yielded a fragment of approximately 800 bp that contained the CMV enhancer, promoter and splice donor site. Following gel isolation, this 800-bp fragment was ligated to a 2900-bp piece of pUC13pML. The fragment required for the construction of pF8CIS was obtained by digestion of the above intermediate plasmid with SalI and HindIII. This 3123-bp piece contained the resistance marker for ampicillin, the origin of replication from pUC13pML, and the control sequences for the CMV, including the enhancer, promoter, and splice donor site.

2. The Ig variable region intron and splice acceptor sequence was constructed using a synthetic oligomer. A 99-mer and a 30-mer were chemically synthesized having the following sequence for the IgG intron and splice acceptor site (Bothwell et al., Cell, 24: 625 (1981)):

```
 1  5'-AGTAGCAAGCTTGACGTGTGGCAGGCTTGA...
31     GATCTGGCCATACACTTGAGTGACAATGA...
60     CATCCACTTTGCCTTTCTCTCCACAGGT...
88     GTCCACTCCCAG-3'
 1  3'-CAGGTGAGGGTGCAGCTTGACGTCGTCGGA-5'
```

DNA polymerase I (Klenow fragment) filled in the synthetic piece and created a double-stranded fragment (Wartell et al., Gene, 9: 307 (1980)). This was followed by a double digest of PstI and HindIII. This synthetic linker was cloned into pUC13 (Veira et al., supra) at the PstI and HindIII sites. The clone containing the synthetic oligonucleotide, labeled pUCIg.10, was digested with PstI. A ClaI site was added to this fragment by use of a PstI-ClaI linker. Following digestion with HindIII a 118-bp piece containing part of the Ig intron and the Ig variable region splice acceptor was gel isolated.

3. The third part of the construction scheme replaced the hepatitis surface antigen 3' end with the polyadenylation site and transcription termination site of the early region of SV40. A vector, pUC.SV40, containing the SV40 sequences was inserted into pUC8 at the BamHI site described in Veira et al., Supra. pUC.SV40 was then digested with EcoRI and HpaI. A 143-bp fragment containing only the SV40 polyadenylation site was gel isolated from this digest. Two additional fragments were gel isolated following digestion of pSVE.8c1D (EPO Pub. No. 160,457). The 4.8-kb fragment generated by EcoRI and ClaI digest contains the SV40-DHFR transcription unit, the origin of replication of pML, and the ampicillin resistance marker. The 7.5-kb fragment produced following digestion with ClaI and HpaI contains the cDNA for Factor VIII. A three-part ligation yields pSVE.8c24D. This intermediate plasmid was digested by ClaI and SalI to give a 9611-bp fragment containing the cDNA for Factor VIII with the SV40 polyadenylation and transcription termination sites followed by the SV40 DHFR transcription unit.

The final three-part ligation to yield pF8CIS used: a) the 3123-bp SalI-HindIII fragment containing the origin of replication, the ampicillin resistance marker and the CMV enhancer, promoter and splice donor; b) the 118-bp HindIII-ClaI fragment containing the Ig intron and splice acceptor; and c) a 9611-bp ClaI-SalI fragment containing the cDNA for Factor VIII, SV40 polyadenylation site, and the SV40 DHFR transcription unit.

Figure 2:
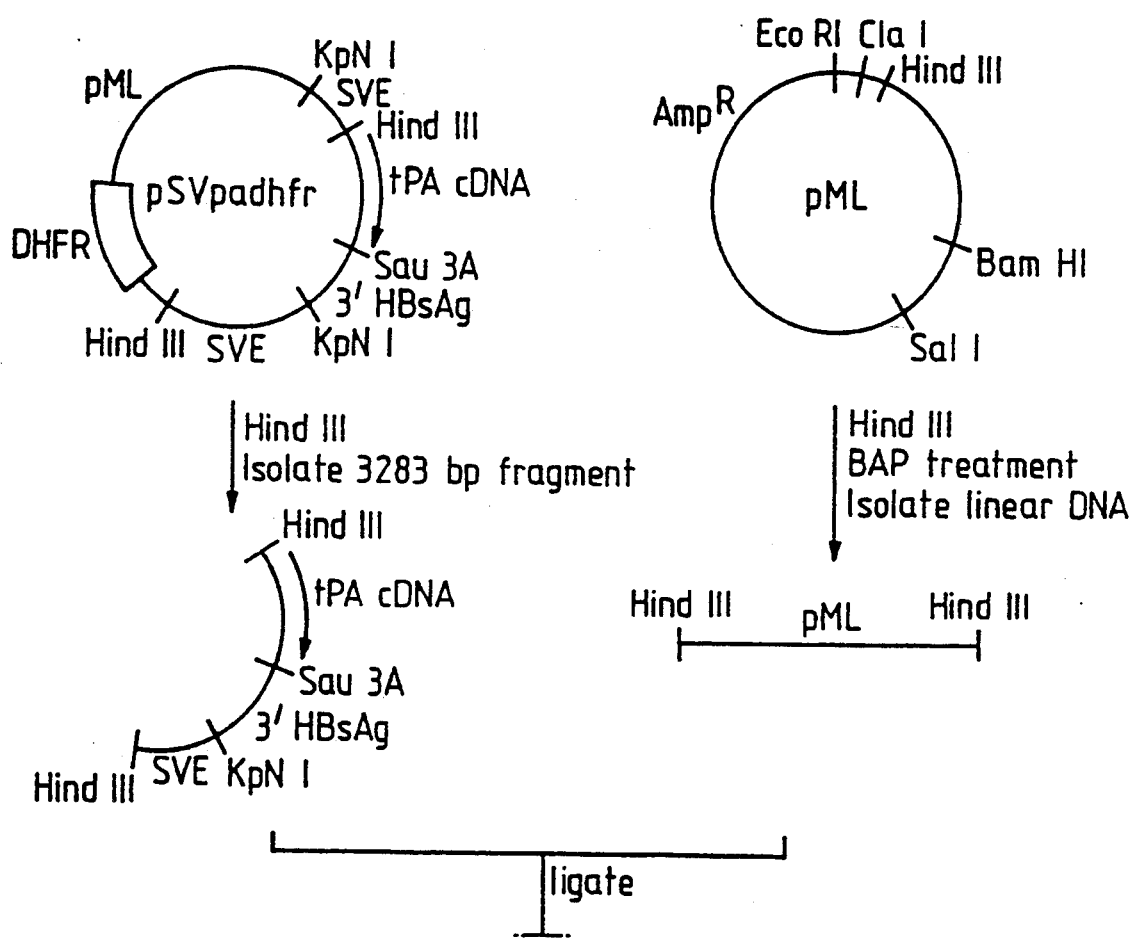
FIGS. 2 and 3 are schematic representations of a suitable method for the preparation of pCISt-PA, together with a description of certain of its prominent restriction sites.
Figure 2:
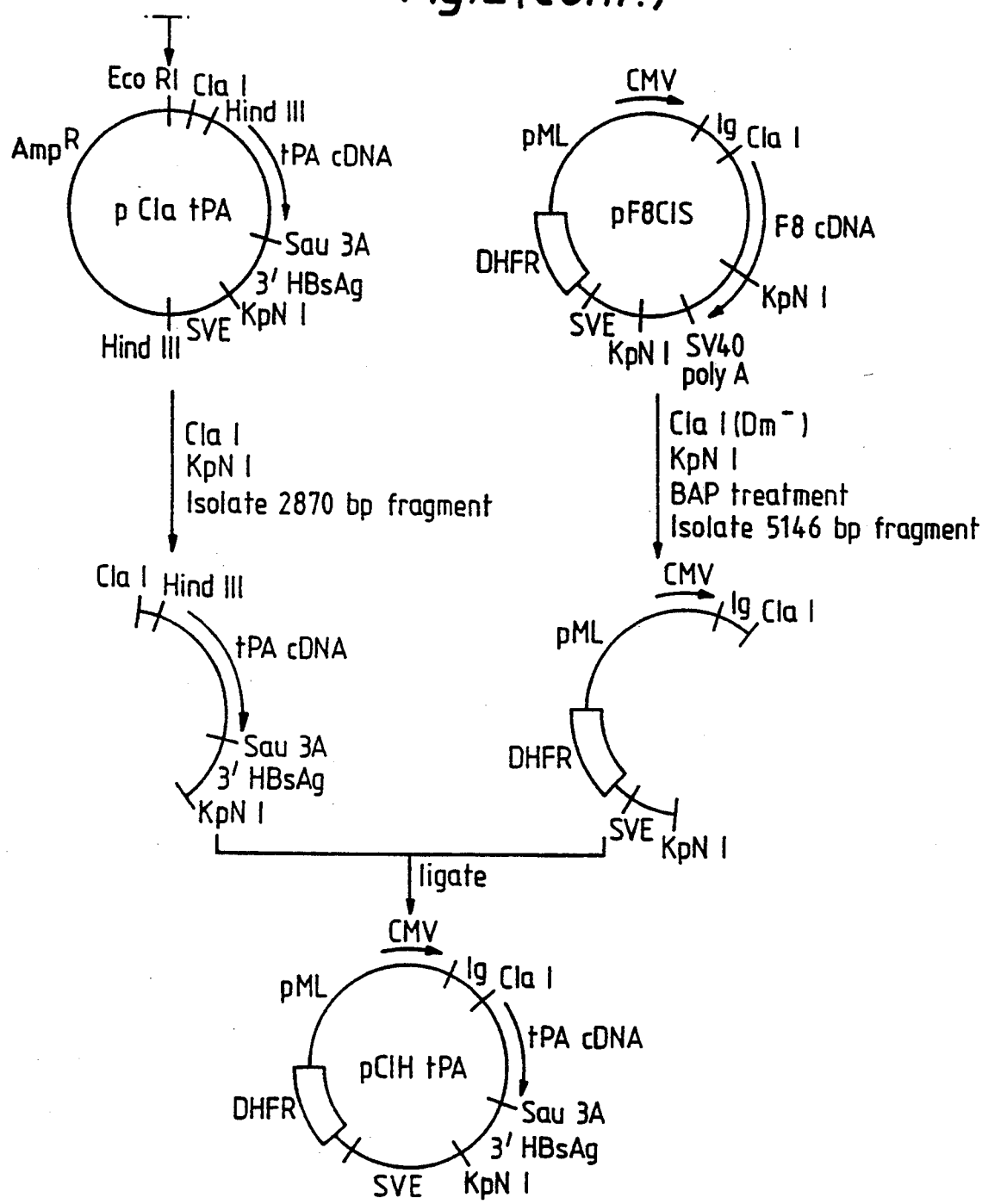

Next, the completion of the construction of plasmid pCIHt-PA from intermediate plasmid pCla t-PA and plasmid pF8CIS (above) was undertaken:

The t-PA cDNA was first cloned into pML to provide a ClaI site at the 5' end of the gene. To do this, a 3238-bp HindIII fragment from pSVpa-DHFR (otherwise referred to as pETPFR, supra) was inserted into the HindIII site of pML (Lusky et al., supra). Colonies were screened for clones that have the 5' end of the cDNA juxtaposed to the ClaI site. The intermediate plasmid was labeled pCLAt-PA. A t-PA cDNA followed by the 3'-polyadenylation regions was isolated as a ClaI-KpnI fragment of 2870 bp. This fragment was ligated to the 5146-bp fragment of pF8CIS. This ClaI-KpnI fragment of the CIS vector provided the 5' control region, a SV40-DHFR transcriptional unit, the ampicillin resistance gene, and the origin region from pML. See FIG. 2.

Expression levels of t-PA were obtained by transfecting CHO or 293 cells with pCIHt-PA, in accordance with methods generally known per se and described supra. Media from the transfected 293 cells, for example, were assayed, demonstrating that pCIHt-PA produced 420 ng/ml of t-PA.

Figure 3:
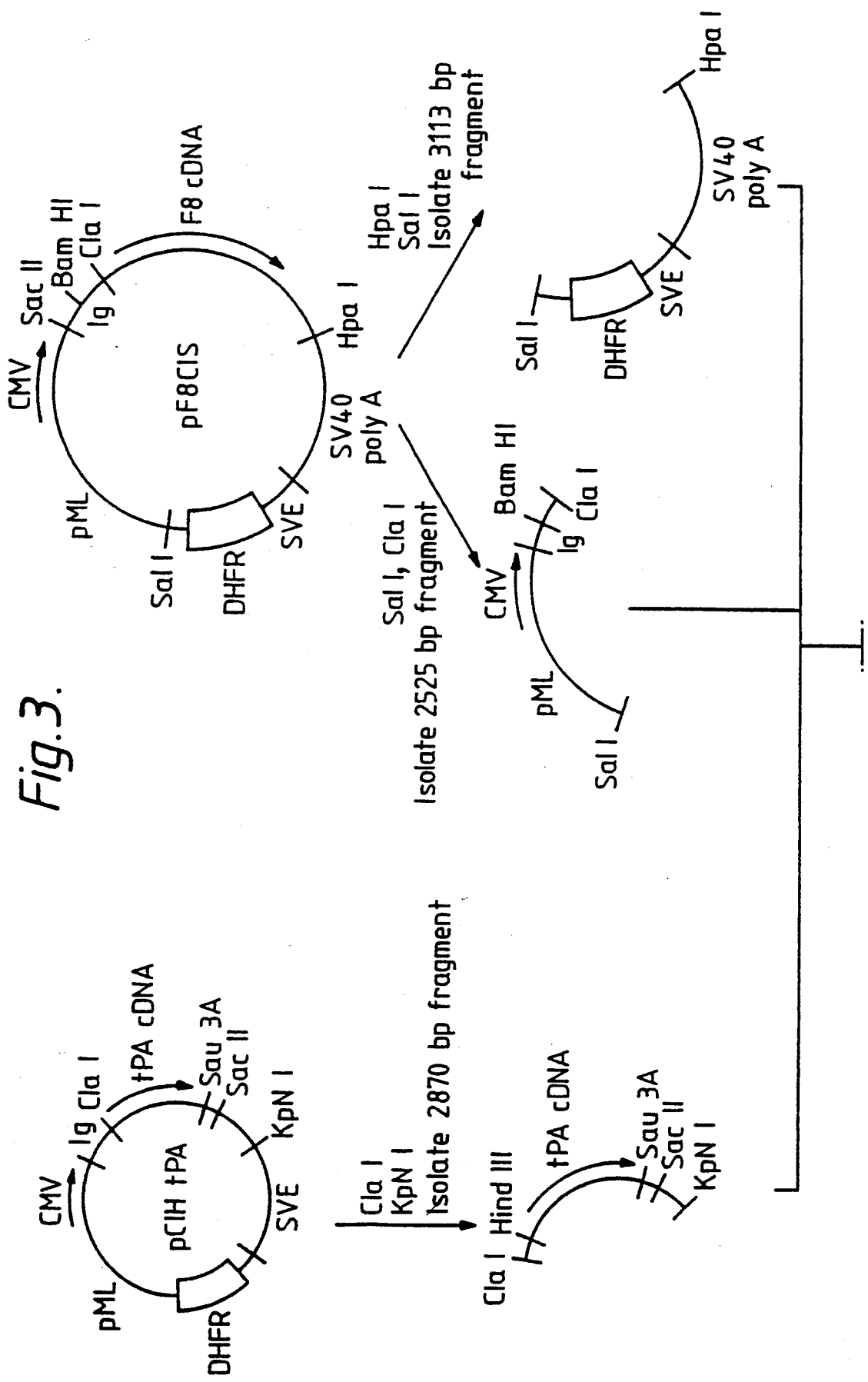
Figure 3:
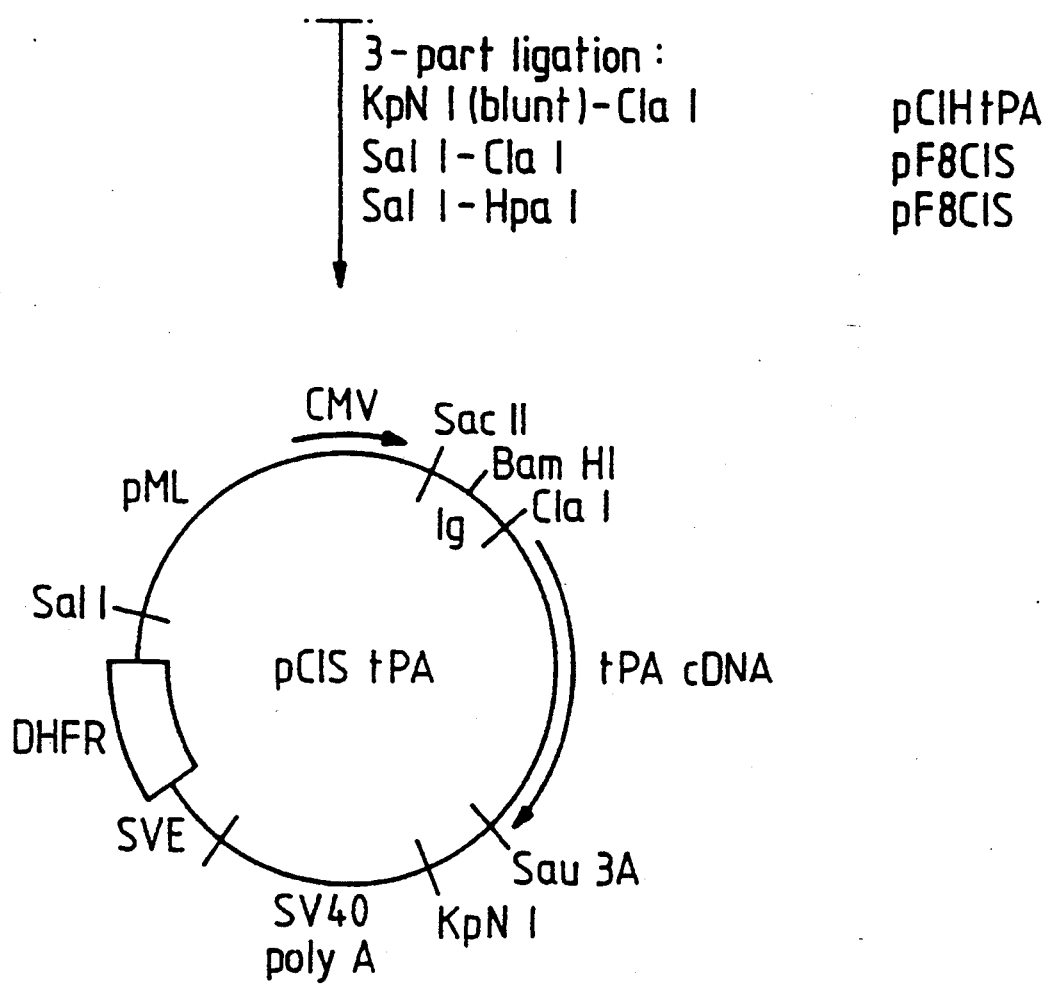

The vector pCISt-PA containing the cytomegalovirus enhancer and promoter, the cytomegalovirus splice donor site and intron, the Ig variable region splice acceptor site, the cDNA encoding t-PA, and the pSV40 polyadenylation sequence was finally constructed as follows:

The starting vectors for this construction were pCIHt-PA and pF8CIS (supra). The latter vector has the same 5' controls as pCIHt-PA, but includes the cDNA for Factor VIII and the SV40 polyadenylation site. SacII was used to cleave 3' of the t-PA cDNA. The resultant 3' overhang was blunted by T4 polymerase. pCIHt-PA was then cut with ClaI. This site separates the chimeric intron cleaving between the CMV intronic sequences and the Ig variable region intron. An 2870-bp fragment was gel isolated from the ClaI treatment. The SV40 polyadenylation site, DHFR, transcription control, bacterial origin of replication, and amp^r gene, as well as the CMV enhancer and promoter and splice donor were isolated from pF8CIS. These elements were isolated into fragments as a 2525-bp SaI-BamHI fragment and a HpaI-SaI and 3113-bp fragment. A three-part ligation of the KpnI (blunt)-ClaI fragment with the HpaI-SaI fragment and SaI to BamHI fragment yields pCISt-PA, which was expressed in both CHO and 293 cells as discussed above for plasmid pCIHt-PA, giving 55 and 3000 ng/ml of t-PA, respectively. See FIG. 3.

b) Final Construction of p7-1H

Figure 4:
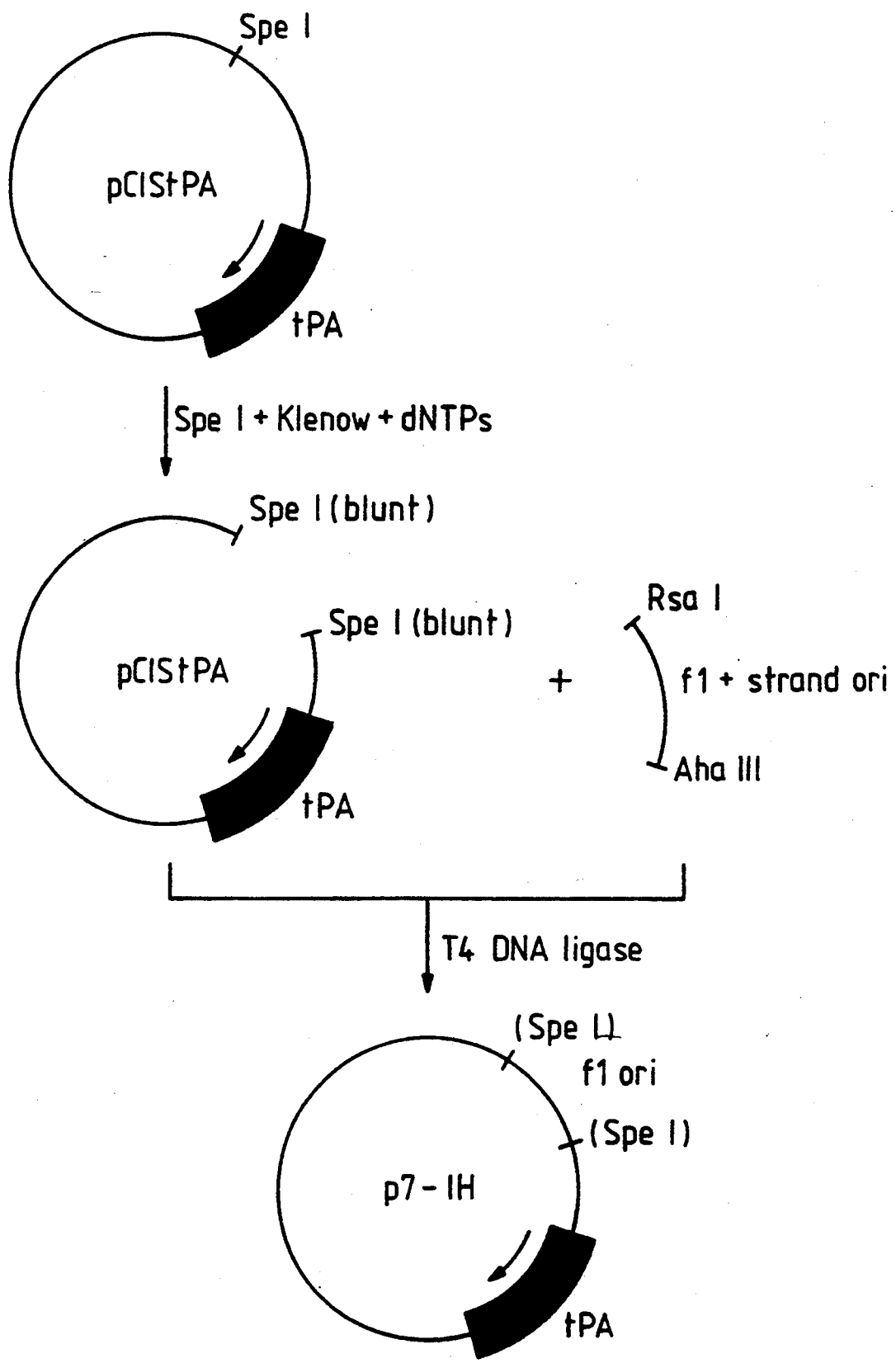
FIG. 4 is a schematic representation of a suitable method for the preparation of p7-1H, together with a description of certain of its prominent restriction sites.

The plasmid pCISt-PA was digested with SpeI, then treated with *E. coli* DNA polymerase I large fragment (Klenow) and deoxyribonucleoside triphosphates to create blunt ends. The resulting linear fragment was ligated, using T4 DNA ligase, to the 0.45kb-RsaI/AhaIII fragment containing the+ strand origin from the single-stranded DNA phage, f1, as described in Zinder et al., Microbiol. Rev., 49: 101 (1985). Ligation products were isolated with the f1 origin inserted in both possible orientations at the SpeI site of the pCISt-PA fragment. A plasmid containing this origin, in such an orientation that the anti-sense strand of the t-PA gene was packaged into virions in the presence of helper phage, was chosen and termed p7-1H. See FIG. 4.

2. Mutagenesis of Expression Plasmid a) Template Preparation

Plasmid p7-1H was introduced into E. coli strain JM101 (ATCC No. 33,876) via $CaCl_2$-mediated transformation. These cells were then infected with the helper virus M13K07 and single-stranded p7-1H DNA was prepared as described by Veira et al., Meth. Enzymol., 153: 3 (1987). Briefly, to 0.3 ml of a saturated culture of transformed cells in 2YT broth was added $10^9$–$10^{10}$ pfu of M13K07 and the mixture was incubated for 15 min. at 37° C. 1.5 ml of fresh 2YT broth, containing 50 μg/ml carbenicillin, was added and the culture was gently shaken for 16 hours at 37° C. After the cells were pelleted, phage and packaged plasmid DNA were harvested, and single-stranded DNA was prepared as described by Anderson, Nucl. Acids. Res., 9: 3015 (1981).

b) Site-directed in vitro Mutagenesis

Mutagenesis on p7-1H was carried out using the oligodeoxyribonucleotide, 5'-CGGAGAGCG-GCACCTGTGCGGGG-3', essentially as described by Zoller et al., Meth. Enzymol., 100: 468 (1983), except that the mutant, with the mutation phe305→his305, was identified by colony hybridization rather than plaque hybridization. Mutations were verified by DNA sequencing directly on the single-stranded plasmid DNA using the dideoxynucleotide chain termination method (Sanger et al., Proc. Natl. Acad. Sci. (U.S.A.) 74: 5463 (1977)).

3. Expression and Purification a) Plasmid Preparation

Transformed cells were grown to saturation in 500-ml LB broth containing 50 μg/ml carbenicillin. Cells were pelleted by centrifugation and resuspended in 40 ml of 50 mM glucose, 10 mM EDTA, 25 mM Tris-HCl (pH 8.0). To this suspension was added 60 ml of 1% sodium dodecyl sulfate, 0.07M NaOH, and the mixture was incubated for 2 min at 25° C., then at 10 min. at 0° C. To this 52 ml of 4M acetic acid, 3M sodium acetate was added and the mixture was incubated for 30 min. at 0° C. This was then centrifuged at 11,500 rpm for 20 min., the supernatant mixed with two volumes of 100% cold ethanol, and the resulting precipitate harvested by centrifugation. The pellet, containing plasmid DNA and RNA, was dried and redissolved in 100 mM Tris (pH 8.0), 10 mM EDTA, 1 μg/ml RNase A. After the resulting solution was clarified by centrifugation, it was adjusted to 0.5 mg/ml in ethidium bromide and an equal weight of CsCl was added. The DNA was then centrifuged in a Beckman VTI65 rotor for 16 hours at 55,000 rpm at 18° C. The DNA band was harvested by side puncture, extracted with n-butanol to remove the ethidium bromide, diluted with $H_2O$, and precipitated by ethanol. DNA was redissolved in 10 mM Tris (pH 8.0), 1 mM EDTA, to a final concentration of 1 mg/ml.

b) Transfection and Expression 293 cells were grown to confluence. Ten μg of t-PA plasmid DNA mutant was mixed with 1 μg of DNA encoding the VA RNA gene (Thimmappaya et al., Cell, 31: 543 (1982)) and dissolved in 500 μl of 1 mM Tris-HCl, 0.1 mM EDTA, 0.227M $CaCl_2$. Added to this (dropwise while vortexing) was 500 μl of 50 mM HEPES (pH 7.35), 280 mM NaCl, 1.5 mM $NAPO_4$, and the precipitate was allowed to form for 10 min. at 25° C. The suspended precipitate was then added to the cells (in 100 mM plate) and allowed to settle for four hours in the incubator. The medium was then aspirated off and 2 ml of 20% glycerol in phosphate-buffered saline (PBS) was added for 30 sec. The cells were washed twice with 5 ml of serum-free medium, then fresh medium was added and the cells were incubated for five days.

For the creation of stable CHO cell lines expressing the t-PA variant, the 1.4 kb BglII/ApaI fragment containing the bulk of the t-PA coding sequences (the BglII site spans codons −1 to 1 of full-length t-PA-encoding DNA and the ApaI site spans codons 465 to 466 of full-length t-PA-encoding DNA) may be ligated to the 6.0-kb BglII/ApaI fragment from the vector pPADHFR-6 (described in EPO Pat. Publn. No. 93,619). The resultant plasmid is then introduced into CHO cells and induced to over-express the t-PA variants by amplifying the coding sequence by means of selection in methotrexate-containing media.

c) Purification

Purification of the t-PA product was accomplished by passing the conditioned medium over a column (1-ml bed volume) of controlled glass beads to which an anti-t-PA goat polyclonal A6 antibody (prepared according to standard methods known per se) had been coupled. Before the medium was loaded, the column was equilibrated with PBS and, after loading, the column was equilibrated with 0.1M Tris-HCl (pH 7.5), 1M NaCl. The t-PA was eluted with 0.1M acetic acid, 0.15M NaCl, 0.02M arginine, 0.01% Tween 80 (pH 2.0), and fractions were immediately neutralized with Tris-base. Fractions were adjusted to 0.01% Tween 80 before pooling. The t-PA was found on a reducing SDS gel to be predominantly (80%) single chain.

B. Biological Assays 1. t-PA Quantitation

Protein concentrations were routinely determined by an ELISA standardized to native-sequence t-PA (See EPO Pat. Publ. 93,619, supra). Protein purity and homogeneity were analyzed by polyacrylamide gel electrophoresis in the presence of sodium dodecyl sulfate (PAGE-SDS) with the buffer system of Laemmli, Nature, 227: 680 (1970). Typically, 7 to 17% gradient gels were used and proteins were visualized with the silver-staining technique of Morrissey, Anal. Biochem., 117: 307 (1981). The t-PA variant prepared as described above was found to be pure and homogeneous by this method.

2. S-2251 Assay

Results for clot lysis and S-2251 assays show averages of several independent observations (clot lysis, two determinations; S-2251, three determinations).

The ability of t-PA to activate plasminogen can be measured in an in vitro assay by preincubating t-PA and plasminogen and then adding the plasmin-specific substrate H-D-valyl-H-leucyl-H-lysine-paranitroanilide (S-2251). The maximum rate of this reaction is observed in the presence of fibrin(ogen) or fragments of fibrin(ogen) that act as stimulators of the reaction.

The plasmin-specific substrate S-2251 was used in a two-stage assay to measure the ability of the sample to activate plasminogen. Fibrinogen could be used as a stimulator by incubating the sample with 0.02 ml of a 20 mg/ml fibrinogen solution in a total volume of 0.12 ml of 0.05M Tris-HCl, 0.12M NaCl, 0.01% Tween 80, pH 7.4.

Glu-plasminogen solution (commercially available), 0.03 ml of a 2.0 mg/ml solution in 0.05M Tris, 0.12M NaCl buffer, pH 8, was then added. After ten min. at 37° C., 0.35 ml of 0.86 mM S-2251 in 0.037M Tris, 0.086

NaCl, 0.007% Tween 80, pH 7.4 was added. This mixture was incubated for five minutes; then the reaction was stopped by the addition of 0.1 ml of 50% glacial acetic acid. Absorbance at 405 nm was measured. The activity was expressed as the change in absorbance per nanogram per minute in the presence of substrate.

The results are that the F305H variant, with fibrinogen, has 78% of the wild-type specific activity, which may be due to the lag before the A405 increases.

3. Clot Lysis

Wild-type and F305H t-PA were assayed for their ability to lyse fibrin in the presence of saturating concentrations of plasminogen, according to the method of Carlsen et al., *Anal. Biochem.*, 168: 428–435 (1988). The in vitro clot lysis assay measures the activity of t-PAs by turbidimetry using a microcentrifugal analyzer. A mixture of thrombin and t-PA test samples is centrifuged into a mixture of fibrinogen and plasminogen to initiate clot formation and subsequent clot dissolution. The resultant profile of absorbance versus time is analyzed to determine the assay endpoint. Activities of the t-PA variants were compared to a standard curve of rt-PA (EPO Publ. No. 93,619, supra). The buffer used throughout the assay was 0.06M sodium phosphate, pH 7.4, containing 0.01% (v/v) Tween 80 and 0.01% (w/v) sodium azide. Human thrombin was at a concentration of 33 units/ml. Fibrinogen (at 2.0 mg/ml clottable protein) was chilled on wet ice to precipitate fibronectin and then gravity filtered. Glu-plasminogen was at a concentration of 1 mg/ml. The analyzer chamber temperature is set at 37° C. The loader is set to dispense 20 $\mu$l of rt-PA (about 62.5 ng/ml to 1.0 $\mu$g/ml) as the sample for the standard curve, or 20 $\mu$l of variant rt-PA at a concentration to cause lysis within the range of the standard curve. Twenty $\mu$l of thrombin was used as the secondary reagent, and 200 $\mu$l of a 50:1 (v/v) fibrinogen: plasminogen mixture as the primary reagent. The absorbance/time program was used with a five-minute incubation time, 340-nm filter, and 90-interval readings.

The results indicate that the F305H variant, using this assay, has about 46% of the clot lysis activity of normal wild-type t-PA.

4. Fibrin Binding

The method for fibrin binding is a modification of the method described by Rijken et al., *J. Biol. Chem.*, 257: 2920 (1982). The t-PA sample to be tested is added to a solution containing 0.05M Tris (pH 7.4), 0.12M NaCl, 0.01% Tween 80, 1 mg/ml human serum albumin, and various concentrations of plasminogen-free fibrin (0, 0.05, 0.1, 0.25, and 0.5 mg/ml). The final volume of the reaction mixture was 1 ml, and the t-PA concentration was 10 ng/ml for each sample. The samples were incubated at 37° C. for 5 min., followed by the addition of 1 unit of thrombin. The samples were then incubated for one hour at 37° C. The clot was removed by centrifugation, and the amount of t-PA remaining unbound in the supernatant was determined by ELISA.

Figure 5:
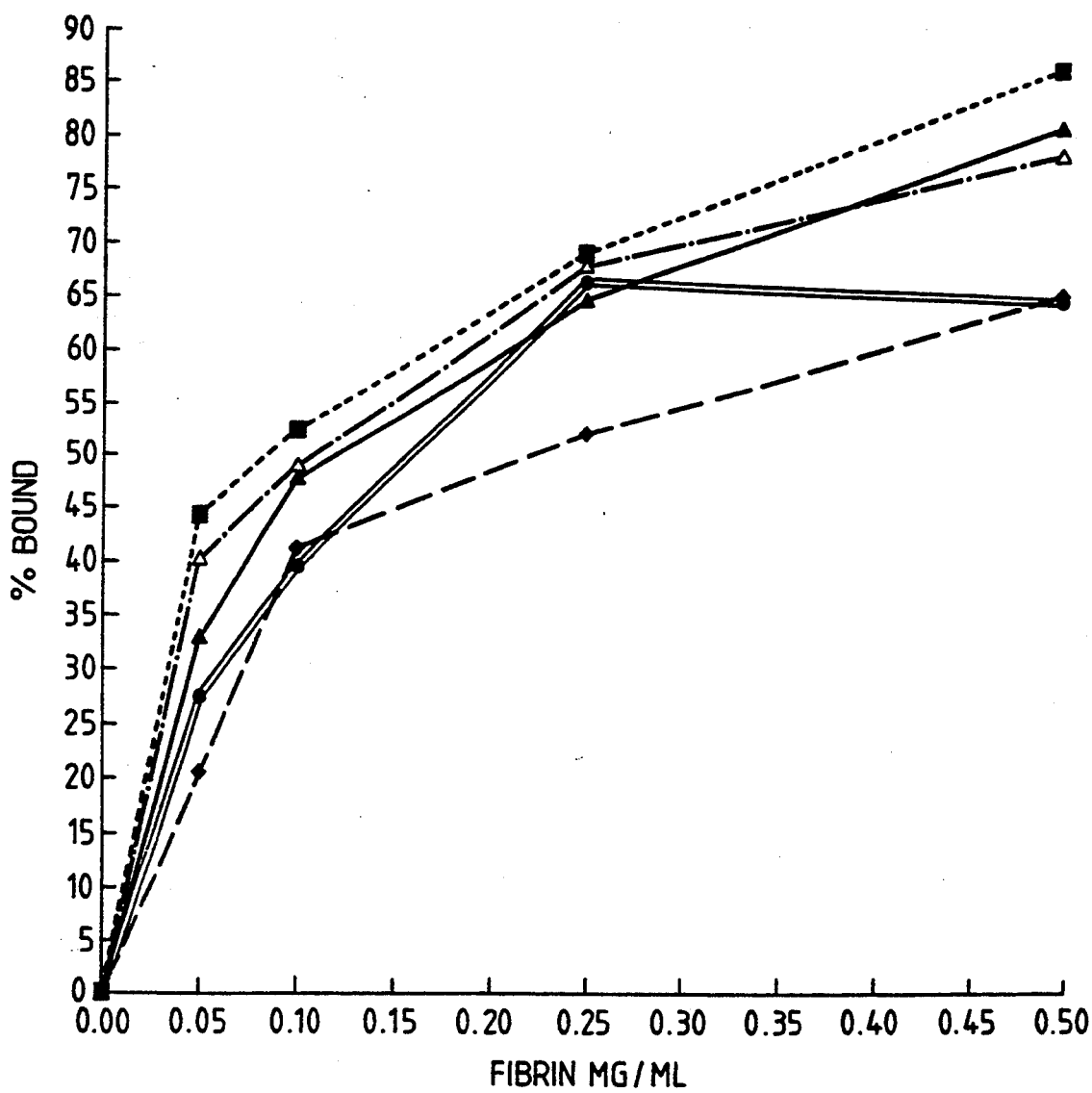
FIG. 5 shows fibrin binding of predominantly one-chain F305H (closed triangles), two-chain F305H (closed circles with double lines), one-chain wild-type t-PA (closed squares), two-chain wild-type t-PA (closed diamonds), and a mixture of one-chain and two-chain wild-type t-PA (open triangles), at a t-PA concentration of 10 ng/ml.

The results (FIG. 5) show that predominantly single-chain F305H t-PA (closed triangles) binds to fibrin under the assay conditions employed almost as well as one-chain wild-type t-PA (closed squares) and the mixture of one-chain and two-chain wild-type t-PA (open triangles). Also, two-chain F305H t-PA (closed circles) binds fibrin at least as well as two-chain wild-type t-PA (closed diamonds).

5. Zymogenic Kinetics by S-2251 a) Preparation of Fibrinogen

Human fibrinogen (Calbiochem) was made plasminogen free by applying it to a lysine-Sepharose column and collecting the flow-through. The resulting fibrinogen pool was degraded by treatment with plasmin-Sepharose at room temperature overnight. The resulting clottability was 7%. The concentration was then adjusted to 1.51 mg/ml.

b) Procedure

The kinetics of the conversion of plasminogen to plasmin by the wild-type t-PA and the F305H t-PA were determined using the chromogenic plasmin substrate S-2251 in the presence of fibrinogen. The wild-type and F305H t-PA molecules were used both in the predominantly one-chain form (obtained by purification as described previously) and in the two-chain, clipped form (obtained by incubation of the predominantly one-chain form with plasmin-Sepharose for one hour at 37° C.).

In the presence of 1.2 $\mu$M plasmin-degraded fibrinogen fragments prepared as described above, the reactions were carried out at plasminogen concentrations from 0.08 to 0.89 $\mu$M and t-PA concentrations of 2.3 to 9.0 nM in 0.12M NaCl, 0.05M Tris, 0.01% Tween 80, pH 7.4. The plasminogen, fibrinogen, and buffer were pre-incubated for three hours at room temperature. The S-2251 was added for a final concentration of 0.9 mM, and the samples were warmed to 37° C. for about 5 minutes. At time zero, the t-PA samples were added, and the absorbance of each sample was read in intervals of 30 seconds for ten minutes at 37° C.

Figure 6:
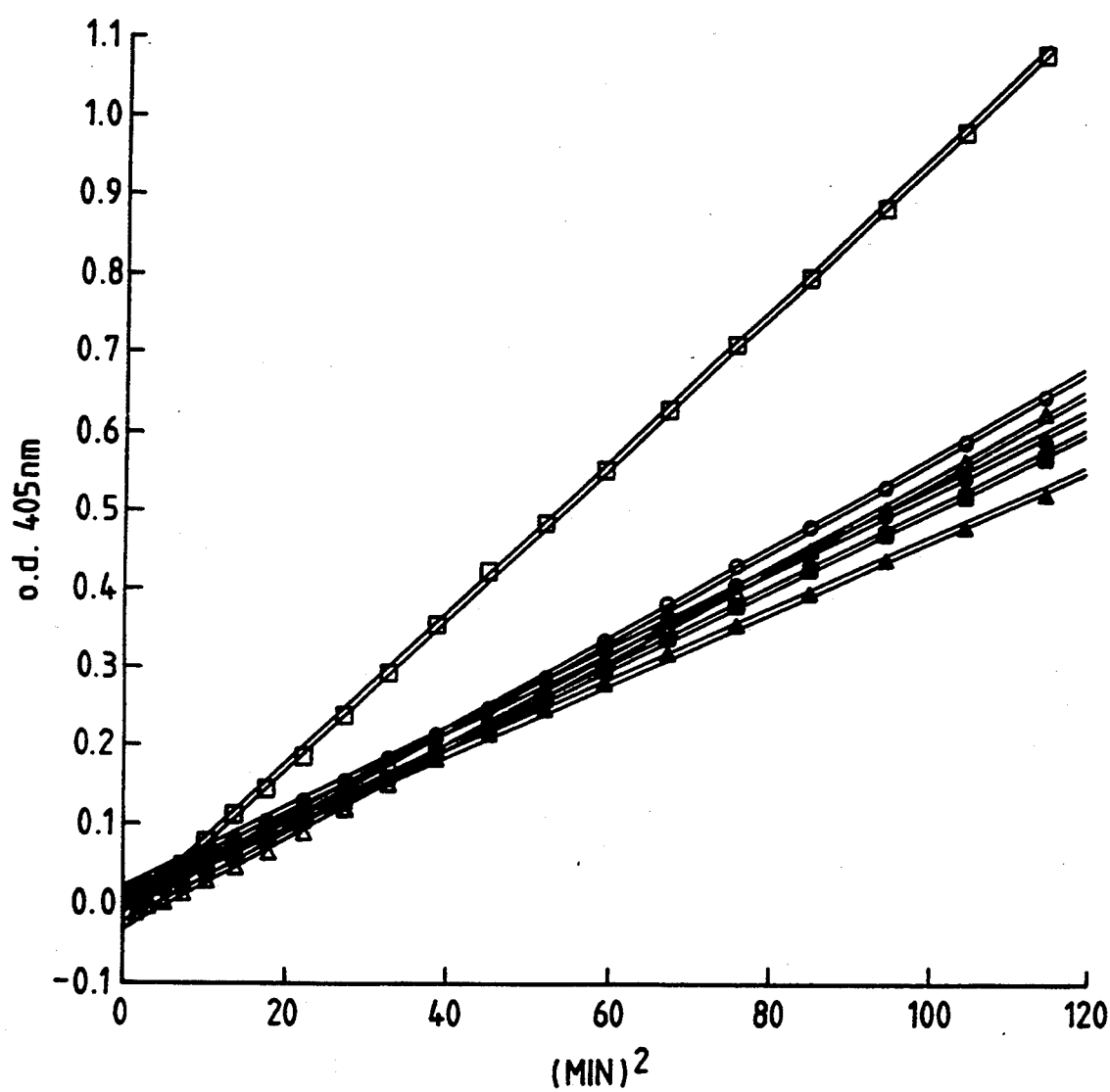
FIGS. 6–9 show plots of the kinetics of the conversion of plasminogen to plasmin in the presence of plasmin-degraded fibrinogen by the predominantly one-chain wild-type t-PA (FIG. 6), the two-chain wild-type t-PA (FIG. 7), the predominantly one-chain F305H t-PA (FIG. 8), and the two-chain F305H t-PA (FIG. 9). The squares, lines, and circles represent various concentrations of plasminogen and t-PA in the assay buffer, which are specified at the end of Example I. In these Figures, the ordinate is the absorbance at 405 nm and the abscissa is the square of the number of minutes at which the absorbance was taken.
Figure 7:
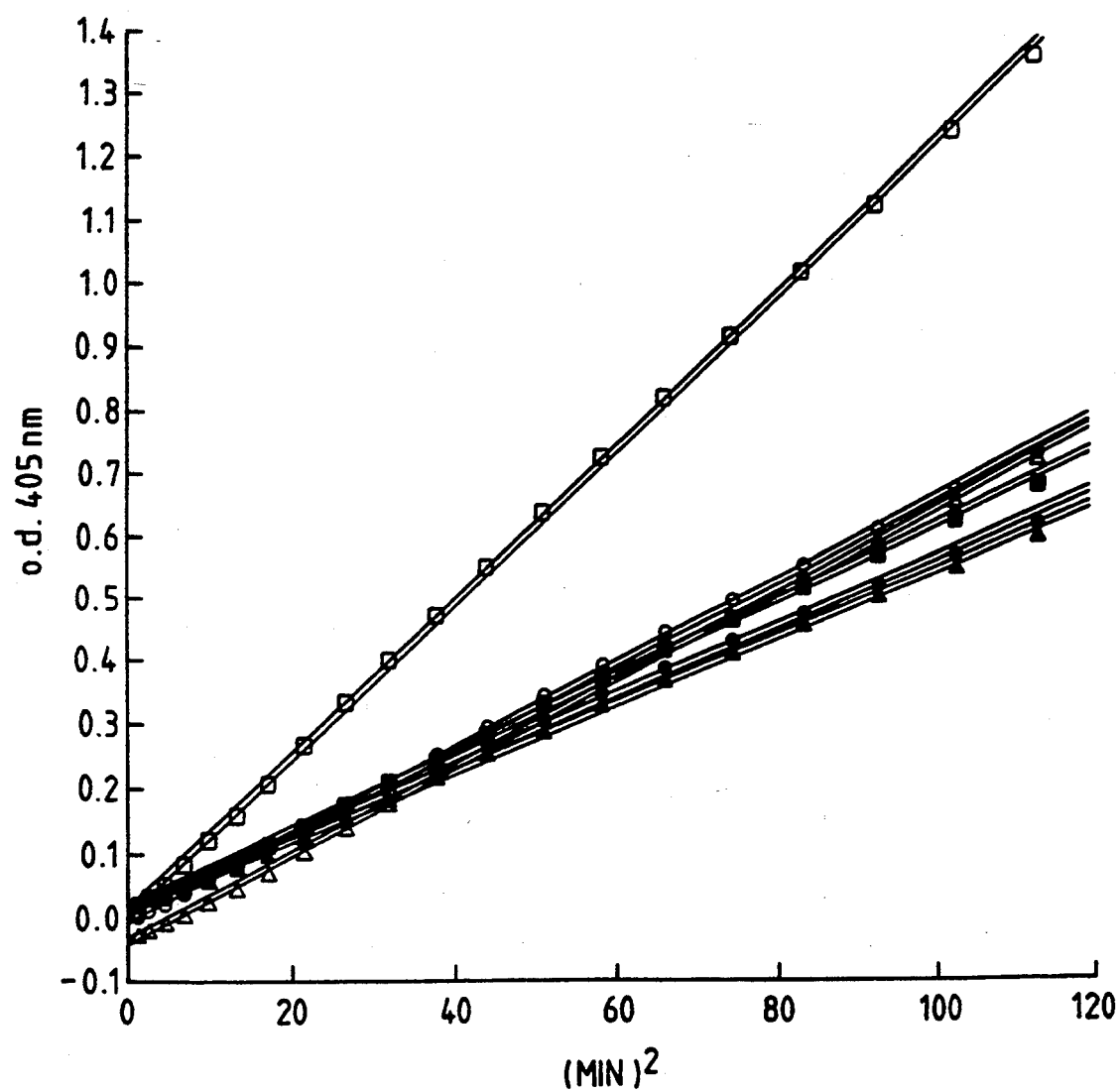
Figure 8:
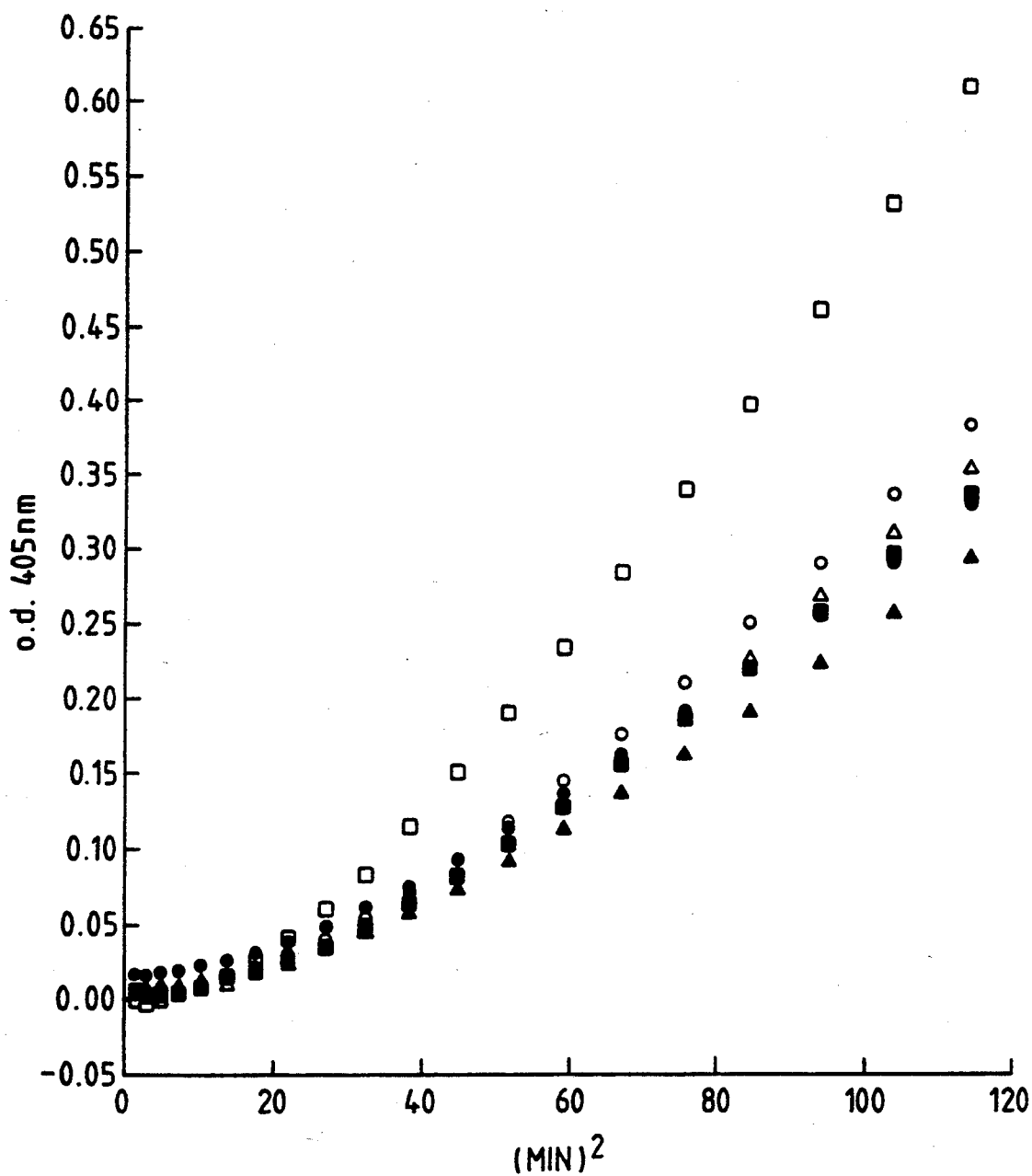
Figure 9:
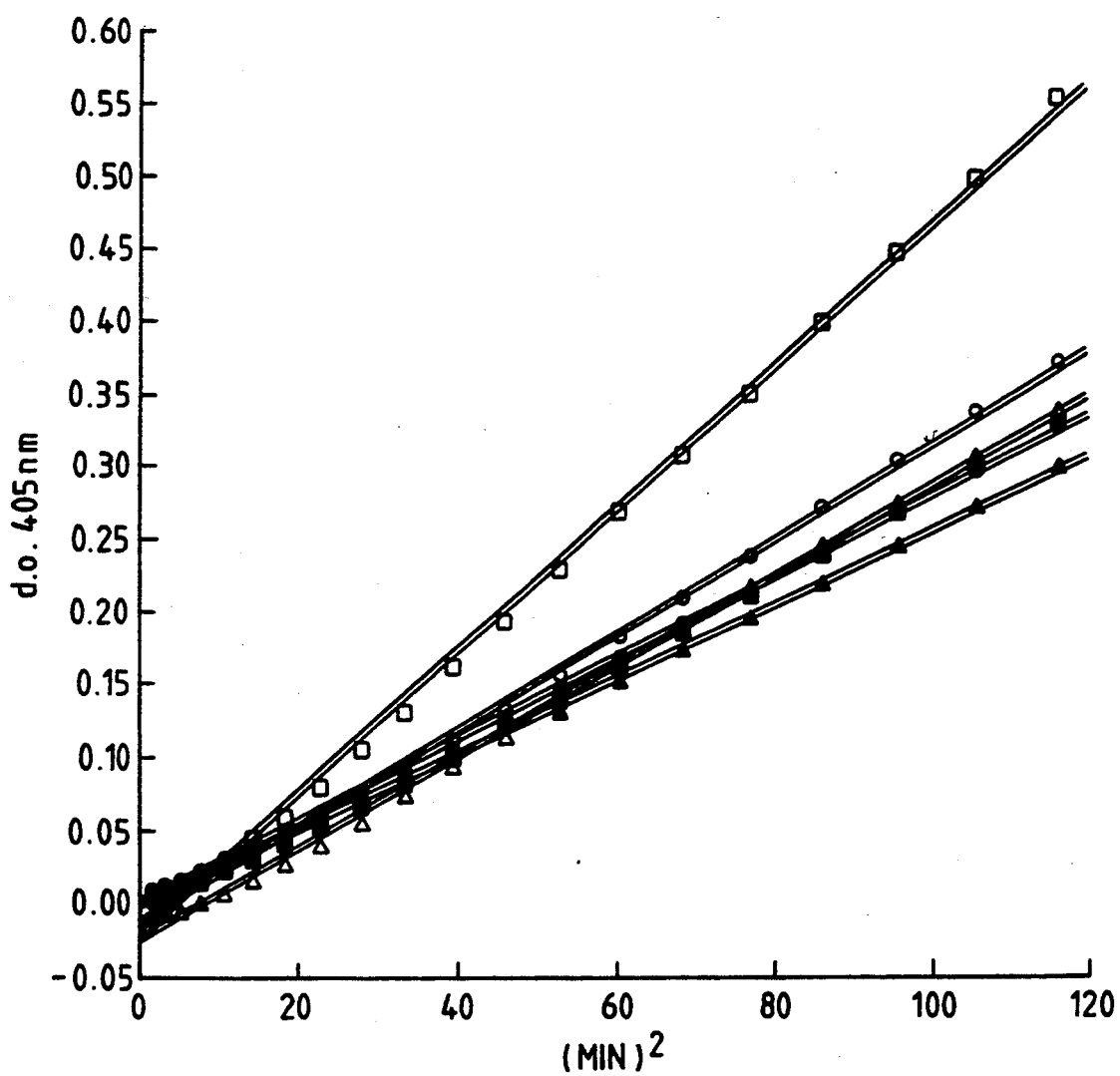

The results are shown in FIGS. 6 and 7 (for wild-type, one-chain and two-chain t-PA, respectively) and in FIGS. 8 and 9 (for F305H, one-chain and two-chain t-PA, respectively). In the figures, the ordinate is the absorbance at 405 nm and the abscissa is the square of the number of minutes at which the absorbances were taken. The closed circles represent 0.09 $\mu$M of plasminogen (and 15.7 nM wild-type two-chain t-PA, 10.8 nM F305H two-chain t-PA, 16.1 nM wild-type one-chain t-PA, and 17.2 nM F305H one-chain t-PA), the closed triangles represent 0.11 $\mu$M of plasminogen (and 11.8 nM wild-type two-chain t-PA, 8.1 nM F305H two-chain t-PA, 12.1 nM wild-type one-chain t-PA, 12.9 nM F305H one-chain t-PA), the closed squares represent 0.16 $\mu$M of plasminogen (and 9.8 nM wild-type two-chain t-PA, 6.7 nM F305H two-chain t-PA, 10.1 nM wild-type one-chain t-PA, 10.8 nM F305H one-chain t-PA), the open circles represent 0.22 $\mu$M of plasminogen (and 7.9 nM wild-type two-chain t-PA, 5.4 nM F305H two-chain t-PA, 8.1 nM wild-type one-chain t-PA, 8.6 nM F305H one-chain t-PA), the open triangles represent 0.44 $\mu$M of plasminogen (and 3.9 nM wild-type two-chain t-PA, 2.7 nM F305H two-chain t-PA, 4.0 nM wild-type one-chain t-PA, 4.3 nM F305H one-chain t-PA), and the open squares represent 0.9 $\mu$M of plasminogen (and 3.9 nM wild-type two-chain t-PA, 2.7 nM F305H two-chain t-PA, 4.0 nM wild-type one-chain t-PA, 4.3 nM F305H one-chain t-PA).

The graphs show that only with the predominantly one-chain F305H variant does the absorbance exhibit a pronounced lag at early times in the reactions, and a rise in activity thereafter. Two-chain F305H variant does not exhibit this lag, but rather appears to have kinetic properties similar to one- or two-chain wild-type t-PA. This behavior demonstrates the zymogenic nature of the F305H variant that is not observed with the wild-type t-PA.

EXAMPLE II

A strategy known as alanine-scanning mutagenesis (ALA-scan), described in Cunningham and Wells, supra, was employed for generation of the t-PA variants evaluated in this example. This method involved the identification of small surface regions of the t-PA protease domain that contain charged amino acid side chains. Without limitation to any one theory, it is believed that either these regions containing clusters of charge, or neighboring regions, or both, are responsible for the interaction of the t-PA molecule with its substrate and various other compounds that may modulate its activity. The charged amino acids in each region (i.e., Arg, Asp, His, Lys, and Glu) were replaced (one region per mutant molecule) with alanine to assess the importance of the particular region to the overall activity of the t-PA molecule. The results are indicated below.

1. Construction of pRK7-t-PA

Plasmid pRK7 was used as the vector for generation of the t-PA mutants. pRK7 is identical to pRK5 (EP Pub. No. 307,247 published Mar. 15, 1989), except that the order of the endonuclease restriction sites in the polylinker region between ClaI and HindIII is reversed. The t-PA cDNA (Pennica et al., Nature, 301: 214 (1983)) was prepared for insertion into the vector by cutting with restriction endonuclease HindIII (which cuts 49 base pairs 5' of the ATG start codon) and restriction endonuclease BalI (which cuts 276 base pairs downstream of the TGA stop codon). This cDNA was ligated into pRK7 previously cut with HindIII and SmaI using standard ligation methodology (Maniatis et al., Molecular Cloning: A Laboratory Manual, Cold Spring Harbor Laboratory, New York, 1982). This construct was named pRK7-t-PA.

2. Site-Directed Mutagenesis of pRK7-t-PA

Site-directed mutagenesis of t-PA cDNA was performed by the method of Taylor et al., Nucl. Acids. Res., 13: 8765 (1985) using a kit purchased from the Amersham Corporation (catalog number RPN 1253). For generation of the desired mutants, oligonucleotides of sequences coding for the desired amino acid substitutions were synthesized and used as primers. These oligonucleotides were annealed to single-stranded pRK7-t-PA that had been prepared by standard procedures (Viera et al., Meth. Enz., 143: 3 (1987)).

A mixture of three deoxyribonucleotide triphosphates, deoxyriboadenosine triphosphate (dATP), deoxyriboguanosine triphosphate (dGTP), and deoxyribothymidine triphosphate (dTTP), was combined with a modified thiodeoxyribocytosine called dCTP($\alpha$S) provided in the kit by the manufacturer of the kit, and added to the single-stranded pRK7-t-PA to which was annealed the oligonucleotide.

Upon addition of DNA polymerase to this mixture, a strand of DNA identical to pRK7-t-PA except for the mutated bases was generated. In addition, this new strand of DNA contained dCTP($\alpha$S) instead of dCTP, which served to protect it from restriction endonuclease digestion. After the template strand of the double-stranded heteroduplex was nicked with an appropriate restriction enzyme, the template strand was digested with ExoIII nuclease past the region that contained the mutagenic oligomer. The reaction was then stopped to leave a molecule that was only partly single-stranded. A complete double-stranded DNA homoduplex molecule was then formed by DNA polymerase in the presence of all four deoxyribonucleotide triphosphates, ATP, and DNA ligase.

The following oligonucleotides were prepared to use as primers to generate pRK7-t-PA molecules using the ALA-scan methodology described above:

5'-GGCTGTACTGGGCCAGGCCGCA-3' (R267A)
5'-GGCAGCCTGCCAGGGGGCGGAGGCGATGGCGGCGAAGAG-3' (D283A,H287A)
5'-CCGCTCTCCGGGCGACGCCGCGGCCGCGGCAAAGAT-3' (K296A,H297A,R298A,R299A)
5'-GCCCCCGCACAGGAACGCCGCTCCGGGCGA-3' (E303A,R304A)
5'-CTCCTGGAAGCAGGCGGCGGCAGA-3' (H322A)
5'-GTGGTGGGGCGGAAACGCCGCCTGGAACGA-3' (E326A,R327A)
5'-CAAGATCACCGTCAGGGCGGCGGGCGGAAA-3' (H331A,H332A)
5'-CTCGCCAGGGACCACCGCGTATGTTGCGCCCAAGAT-3' (R339A,R342A)
5'-TTTTTCGACTTCAAATGCCTGCGCCGCCGCGCCAGGGAC-3' (E347A,E348A,E349A,K351A)
5'-CTTATGGACAATGTATGCTGCGACTGCAAATTTCTG-3' (E353A,E355A,K356A)
5'-AGTGTCATCATCGAATGCCGCAGCGACAATGTA-3' (H360A,K361A,E362A)
5'-GTCATTGTCGTAAGTGGCAGCGAATTCCTT-3' (D364A,D365A,D366A)
5'-CTGCAGCAGCGCAATGGCATTGGCGTAAGTGTC-3' (D369A,D371A)
5'-CTCCTGGGCACAGGCGGACGAAGCCGATGCCAGCTGCAG-3' (K378A,D380A,R383A)
5'-AAGGCACACAGTGGCGACCACGCTGCTCGCCTGGGCACA-3' (E387A,R392A)
5'-ACACTCCGTCCAGGCCGGCAGCTGCAGGGCCGCCGGGGG-3' (D400A,D405A)
5'-GGAGAGCTCACAGGCCGTCCAGTC-3' (E408A)
5'-GTAGCCGGAGAGGGCACACTCCGT-3' (E410A)
5'-AGGAGACAAGGCCGCAGCCGCGCCGTAGCC-3' ((K416A,H417A,E418A)
5'-TCTGACATGAGCCGCCGCCAGCGCCGCCGAATAGAA-3' (E426A,R427A,K429A,E430A)
5'-GGATGGGTACAGTGCGACAGCAGCCTCCTT-3' (H432A,R434A)
5'-TTGTGATGTGCAGGCGCTGGATGG-3' (R440A)
5'-GTCGGTGACTGTTGCGTTAAGTAAAGCTTGTGATGT-3' (H445A,R449A)
5'-ACACAGCATGTTGGCGGTGACTGTTGCGTTAAGTAA-3' (R449A,D453A)
5'-GGGCCCGCCGCTCGCAGTGGCTCCAGCACA-3' (D460A,R462A)
5'-GCCCTGGCAGGCGGCGGCCAAGTTTGC-3' (H471A,D472A)
5'-GGGGCCTCCCGAAGCGCCCTGGCA-3' (D477A)
5'-CACCAAAGTCATGGCGCCAGCGTTCAGACA-3' D487A,R489A)
5'-CACACCCGGGACAGCCGCCTGTCCACA-3' (K505A,D506A)
5'-GTAGTTGGTAACGGCTGTGTACAC-3' (K513A)
5'-CGGTCGCATGTTGGCAGCAATCCAGGCTAGGTAGTT-3' (D519A,R522A,D523A)
5'-TCCTGGTCACGGTGCCATGTTGGCACGAATCCA-3' (D523A,R526A)

3. Bacterial Transformation and DNA Preparation

The mutant t-PA constructs generated using the protocol above were transformed into *E. coli* host strain MM294tonA using the standard CaCl$_2$ procedure (Maniatis et al., supra) for preparation and transformation of competent cells. MM294tonA (which is resistant to T1 phage) was prepared by the insertion and subsequent imprecise excision of a Tn10 transposon into the tonA gene. This gene was then inserted, using transposon insertion mutagenesis (Kleckner et al., *J. Mol. Biol.*, 116: 125–159 (1977)), into *E. coli* host MM294 (ATCC 31,446).

DNA was extracted from individual colonies of bacterial transformants using the standard miniprep procedure of Maniatis et al., supra. The plasmids were further purified by passage through a Sepharose CL6B spin column, and then analyzed by sequencing and by restriction endonuclease digestion and agarose gel electrophoresis.

One of these transformants containing the plasmid encoding the K296A, H297A, R298A, R299A mutant, and designated pTPA33-2, was deposited with the American Type Culture Collection on Jul. 18, 1989 as ATCC No. 68,059.

4. Transfection of Human Embryonic Kidney 293 Cells (Small-Scale)

293 cells were grown to 70% confluence in 6-well plates. 2.5 μg of t-PA plasmid DNA mutant was dissolved in 150 μl of 1 mM Tris-HCl, 0.1 mM EDTA, 0.227M CaCl$_2$. Added to this (dropwise while vortexing) was 150 μl of 50 mM HEPES buffer (pH 7.35), 280 mM NaCl, 1.5 mM NaPO$_4$, and the precipitate was allowed to form for ten min. at 25° C. The suspended precipitate was then added to the cells in the individual wells in a 6-well plate and allowed to settle for four hours in the incubator. The medium was then aspirated off and 1 ml of 20% glycerol in PBS was added for 30 sec. The cells were washed twice, first with 3 ml, then with 1 ml, of serum-free medium. Then 3 ml of fresh medium was added and the cells were incubated for five days. The medium was then collected and assayed.

When single-chain t-PA was required, the procedure was as described above except that plasminogen-depleted serum was used during the growth phase of the cells.

5. Transfection of Human Embryonic Kidney 293 Cells (Large Scale)

For large-scale purification of the K296A, H297A, R298A, R299A variant, useful for production in significant quantities, the transfection procedure used was obtained from *Current Protocols in Molecular Biology*, Ausubel et al., eds. (Wiley Interscience, 1988) and modified slightly as follows: A suspension of human embryonic kidney 293 cells was grown in a cell culture medium and concentrated by pelleting. The pellet was resuspended to a concentration of about $10^8$ cells per milliliter and the cells were washed as necessary in serum-free media. The DNA-dextran solution was added at a concentration of about 250 μg of DNA per 500 ml of cells, and this mixture was incubated with mild agitation at 37° C. for up to 90 minutes. DMSO was added to a final concentration of ten percent and, after about two minutes, fresh medium was added to dilute the cells to about $10^6$ per milliliter. Cells were then incubated for up to seven days, after which time the supernatant was collected.

Purification of this mutant was accomplished by passage of the supernatant over a column of glass beads coupled to anti-t-PA goat polyclonal A6 antibody. The column had been preconditioned with PBS. After the supernatant was loaded, the column was equilibrated with a Tris-saline buffer [0.1M Tris.HCl (pH 7.5) and 1M NaCl]. The t-PA variant was then eluted with 0.1M acetic acid, 0.15M NaCl, 0.02M arginine, and 0.01% Tween 80. Fractions were immediately neutralized with Tris base and adjusted to 0.01% Tween 80.

6. Biological Assays

A. t-PA Quantitation

The amount of t-PA present in the cell culture supernatants was determined by the ELISA procedure using polyclonal antibodies prepared against wild-type t-PA.

B. S-2288 Assay

The S-2288 assay was used to measure the proteolytic activity of the mutants in both the one- and two-chain forms. This assay is a direct assay for t-PA proteolytic activity; t-PA cleaves the bond between the small peptide and the paranitroanilide chromophore.

Standard curve samples were prepared by diluting wild-type rt-PA with cell culture media. The standard curve samples and rt-PA mutant samples were added to the wells of a microtiter plate. If the assay was used to measure the activity of two-chain rt-PA, an incubation step with human plasmin was included in the procedure. Human plasmin (KabiVitrum) was added to a final concentration of 0.13 CU (casein units)/ml. The samples were incubated for 90 minutes at room temperature. For assaying the samples in the single-chain form, the plasmin solution was replaced by PBS and the 90-minute incubation was omitted.

Aprotinin [Sigma, approximately 14 TIU (trypsin inhibitor unit)/mg] was added to a final concentration of 72 μg/ml to inhibit the plasmin activity, and the samples were incubated at room temperature for 15 minutes. A 2.16 mM solution of S-2288 was diluted to 1.45 mM with 0.1M Tris, 0.106 mM NaCl, 0.02% sodium azide, pH 8.4, and 100 μl of this solution was added to each well of the microtiter plate (final volume in each well was 200 μl). Color development was monitored at 405 nm. The slope of the absorbance vs. time curve for each standard and sample was determined. A standard curve was prepared by plotting the slope of the absorbance vs. time curve as a function of rt-PA concentration for the rt-PA standards. The relative activity concentration of the mutants was then determined from the standard curve. The activity concentration of each mutant was divided by the concentration for the mutant obtained in the rt-PA ELISA, and the resulting specific activities were expressed relative to wild-type t-PA, which was assigned a value of 1.0.

The data are averages of two assays and are presented as activity relative to wild-type rt-PA in Table I. The results show that for all mutants presented, the two-chain form is more active (at least 1.5-fold, up to nearly 60-fold) than the one-chain form, relative to wild-type rt-PA, indicating that each of these mutants may be considered zymogenic in this assay.

TABLE I

Zymogens in the S-2288 Assay

| Mutation | Activity Relative to wt rt-PA (where wt is 1.0; () indicates experimental error) | | fold difference |
|---|---|---|---|
| | one-chain | two-chain | |
| R267A | 0.33 (0.03) | 0.85 (0.13) | 2.6 |
| D283A,H287A | 0.08 (0.11) | 0.60 (0.23) | 7.5 |
| R339A,R342A | 0.01 (0.01) | 0.52 (0.01) | 52 |

TABLE I-continued

Zymogens in the S-2288 Assay

| | Activity Relative to wt rt-PA (where wt is 1.0; () indicates experimental error) | | |
|---|---|---|---|
| Mutation | one-chain | two-chain | fold difference |
| E347A,E348A,E349A,K351A | 0.01 (0.01) | 0.49 (0.18) | 49 |
| K416A,H417A,E418A | 0.01 (0.01) | 0.59 (0.01) | 59 |
| E426A,R427A,K429A,E430A | 0.01 (0.01) | 0.33 (0.04) | 33 |
| H432A,R434A | 0.08 (0.01) | 0.71 (0.08) | 8.9 |
| R440A | 0.53 (0.03) | 0.78 (0.04) | 1.5 |

C. S-2251 Assay

This assay is an indirect assay for t-PA activity. In this assay, plasminogen is converted to plasmin by the action of t-PA, and plasmin cleaves the S-2251 substrate to release the paranitroanilide chromophore. Production of this chromophore is then measured over time.

1. Fibrin-Stimulated S-2251 Assay

Standard curve samples were prepared as described for the S-2288 assay. Samples assayed in the two-chain form were incubated with plasmin-Sepharose. Plasmin-Sepharose was prepared by coupling approximately 20.8 CU of human plasmin (KabiVitrum) to 1 ml of cyanogen bromide activated Sepharose (Pharmacia). The plasmin-Sepharose (50 µl of a 5% slurry) was incubated with shaking for 90 min. at room temperature with 150 µl of sample. Following the incubation, the resin was removed by centrifugation, and 10 µl of sample were added to the wells of a microtiter plate.

For samples assayed in the one-chain form, 50 µl of cell culture media were added in place of resin, and the incubation step was omitted. Human thrombin (10 µl of a 42 unit/ml solution) was added to each well. The reaction in each well was started by the addition of a cocktail (130 µl) composed of 28 µl of human Glu-plasminogen (5.3 µM); 10 µl of plasminogen-free human fibrinogen (10 µM); 30 µl of 3 mM S-2251 (KabiVitrum); and 62 µl of PBS. Color development was monitored at 405 nm, and the absorbance at the reference wavelength of 492 nm was subtracted from each time point. The slope of the absorbance vs. time squared curve was determined for each standard and mutant sample. A standard curve was prepared by plotting the slope of the absorbance vs. time squared curve as a function of rt-PA concentration for the rt-PA standards. The determination of the relative specific activity for the mutants was as described for the S-2288 assay.

2. Fibrinogen-Stimulated S-2251 Assay

This assay was performed as described for the fibrin-stimulated S-2251 assay except that PBS was substituted for the thrombin.

3. Plasma Clot S-2251 Assay

The standard curve sample preparation and the conversion of one-chain rt-PA to two-chain rt-PA using plasmin-Sepharose were as described for the fibrin-stimulated S-2251 assay. Human thrombin (10 µl of a 31 µg/ml solution) was added to each well of the microtiter plate. The standard and mutant samples (40 µl) were added to the plate and the reaction was started by adding 100 µl of a mixture of 90 µl of acid citrate dextrose human plasma and 10 µl of 9.1 mM S-2251 (KabiVitrum). Color development was monitored at 405 nm and the absorbance at the reference wavelength of 492 nm was subtracted from each time point. The analysis of the data was as described for the fibrin-stimulated S-2251 assay.

4. Plasma S-2251 Assay

This assay was performed as described for the plasma clot S-2251 assay except that PBS was substituted for the thrombin.

Mutants were assayed for zymogenic qualities using the fibrin-dependent and plasma clot-dependent assays, and the results, relative to wild-type, are shown in Tables II and III, respectively. Values for mutants in the single-chain form are averages of two determinations. Values for mutants in the two-chain form are averages of four determinations.

TABLE II

Zymogens in the Fibrin-Dependent S-2251 Assay

| | Activity Relative to wt rt-PA (where wt is 1.0; () indicates experimental error) | | |
|---|---|---|---|
| Mutation | one-chain | two-chain | fold difference |
| K296A,H297A,R298A,R299A | 1.26 (0.02) | 2.82 (0.32) | 2.2 |
| E303A,R304A | 1.38 (0.04) | 2.13 (0.29) | 1.5 |
| H331A,H332A | 1.29 (0.04) | 2.19 (0.68) | 1.7 |
| R339A,R342A | 0.38 (0.07) | 1.04 (0.11) | 2.7 |
| K416A,H417A,E418A | 0.21 (0.04) | 0.96 (0.09) | 4.6 |
| E426A,R427A,K429A,E430A | 0.14 (0) | 0.76 (0.07) | 5.4 |
| H432A,R434A | 0.16 (0.08) | 0.99 (0.13) | 6.2 |
| D460A,R462A | 0.68 (0.04) | 1.04 (0.08) | 1.5 |

TABLE III

Zymogens in the Plasma Clot-Dependent S-2251 Assay

| | Activity Relative to wt rt-PA (where wt is 1.0; () indicates experimental error) | | |
|---|---|---|---|
| Mutation | one-chain | two-chain | fold difference |
| D283A,H287A | 0.53 (0.01) | 0.82 (0.04) | 1.6 |
| K296A,H297A,R298A,R299A | 0.42 (0) | 1.29 (0.20) | 3.1 |
| E303A,R304A | 0.90 (0.03) | 1.34 (0.10) | 1.5 |
| H331A,H332A | 1.09 (0.09) | 1.61 (0.68) | 1.5 |
| R339A,R342A | 0.19 (0.03) | 0.79 (0.10) | 4.2 |
| E347A,E348A,E349A,K351A | 0.38 (0.05) | 0.97 (0.10) | 2.6 |
| D364A,D365A,D366A | 0.88 (0.03) | 1.46 (0.15) | 1.7 |
| K416A,H417A,E418A | 0.19 (0.05) | 0.77 (0.05) | 4.1 |
| E426A,R427A,K429A,E430A | 0.11 (0.01) | 0.66 (0.12) | 6 |
| H432A,R434A | 0.05 (0.01) | 0.38 (0.05) | 7.6 |
| H445A,R449A | 0.80 (ND)* | 1.19 (0.11) | 1.5 |
| R449A,D453A | 0.79 (0.01) | 1.22 (0.13) | 1.5 |
| D460A,R462A | 0.21 (0.01) | 0.32 (0.02) | 1.5 |
| D477A | 0.11 (0.02) | 0.25 (0.08) | 2.3 |

*ND = Not Determined

A summary of the data in Tables I–III, indicating for which assay each mutant displays zymogenicity, is shown below, in Table IV:

TABLE IV

| | Zymogen in | | |
|---|---|---|---|
| Mutation | S-2288 | Fn* 2251 | Plasma Clot 2251 |
| R267A | X | | |
| D283A,H287A | X | | X |
| K296A,H297A,R298A,R299A | | X | X |
| E303A,R304A | | X | X |
| H331A,H332A | | X | X |
| R339A,R342A | X | X | X |
| E347A,E348A,E349A,K351A | X | | X |
| D364A,D365A,D366A | | | X |

TABLE IV-continued

| | Zymogen in | | |
|---|---|---|---|
| Mutation | S-2288 | Fn* 2251 | Plasma Clot 2251 |
| K416A,H417A,E418A | X | X | X |
| E426A,R427A,K429A,E430A | X | X | X |
| H432A,R434A | X | X | X |
| R440A | | | X |
| H445A,R449A | | | X |
| R449A,D453A | | | X |
| D460A,R462A | | X | X |
| D477A | | | X |

*Fn = fibrin.

The zymogenic t-PA variants listed in Table IV were analyzed in the S-2251 fibrin specificity assay and/or S-2251 plasma clot specificity assay in both the one-chain and two-chain forms. The results for one-chain and two-chain t-PA variants are shown in Tables V and VI, respectively.

A summary of the data in Tables V and VI is shown below in Table VII. It can be seen that each of the zymogenic rt-PA variants from Table IV is also fibrin- and/or plasma clot-specific relative to wild-type t-PA. An X indicates a ratio of fibrin to fibrinogen or plasma clot to plasma of >1.5 as measured in the S-2251 assay and reported in Tables V and VI.

TABLE V activities are relative to wt rt-PA (where wt is 1.0).
FIBRIN- AND PLASMA CLOT-SPECIFICITY OF rt-PA VARIANTS (ONE-CHAIN)

| | Mutant | Fg | Fb | Fb/Fg | Pl | PC | PC/Pl |
|---|---|---|---|---|---|---|---|
| AVE | R267A | 0.53 | 0.92 | 1.74 | 0.24 | 0.71 | 3.00 |
| SD | | (0.00) | (0.01) | | (0.01) | (0.09) | |
| AVE | D283A, | 0.59 | 0.78 | 1.32 | 0.19 | 0.53 | 2.76 |
| SD | H287A | (0.02) | (0.05) | | (0.07) | (0.01) | |
| AVE | K296A, | 0.29 | 1.26 | 4.40 | 0.14 | 0.42 | 3.00 |
| SD | H297A, R298A, R299A | (0.05) | (0.02) | | (0.03) | (0.00) | |
| AVE | E303A, | 0.68 | 1.38 | 2.04 | 0.35 | 0.90 | 2.61 |
| SD | R304A | (0.09) | (0.04) | | (0.01) | (0.03) | |
| AVE | H331A, | 1.19 | 1.29 | 1.08 | 1.12 | 1.09 | 0.97 |
| SD | H332A | (0.06) | (0.04) | | (0.13) | (0.09) | |
| AVE | R339A, | 0.34 | 0.38 | 1.12 | 0.02 | 0.19 | 9.50 |
| SD | R342A | (0.00) | (0.07) | | (0.03) | (0.03) | |
| AVE | E347A, | 0.50 | 0.87 | 1.75 | 0.13 | 0.38 | 2.88 |
| SD | E348A, E349A, K351A | (0.09) | (0.15) | | (0.04) | (0.05) | |
| AVE | D364A, | 0.66 | 1.50 | 2.27 | 0.28 | 0.88 | 3.14 |
| SD | D365A, D366A | (0.03) | (0.04) | | (0.04) | (0.03) | |
| AVE | K416A, | 0.34 | 0.21 | 0.60 | 0.10 | 0.19 | 1.95 |
| SD | H417A, E418A | (0.01) | (0.04) | | (0.04) | (0.05) | |
| AVE | E426A, | 0.21 | 0.14 | 0.68 | 0.07 | 0.11 | 1.50 |
| SD | R427A, K429A, E430A | (0.01) | (0.00) | | (0.01) | (0.01) | |
| AVE | H432A, | 0.16 | 0.16 | 1.00 | 0.08 | 0.05 | 0.60 |
| SD | R434A | (0.01) | (0.08) | | (0.01) | (0.01) | |
| AVE | R440A | 0.62 | 1.02 | 1.64 | 0.48 | 0.86 | 1.81 |
| SD | | (0.08) | (0.18) | | (0.04) | (0.10) | |
| AVE | H445A, | 0.52 | 1.12 | 2.15 | 0.24 | 0.80 | 3.33 |
| SD | R449A | | | | | | |
| AVE | R449A, | 0.58 | 1.16 | 2.00 | 0.28 | 0.79 | 2.87 |
| SD | D453A | (0.01) | (0.11) | | (0.01) | (0.01) | |
| AVE | D460A, | 0.13 | 0.68 | 5.19 | 0.10 | 0.21 | 2.16 |
| SD | R462A | (0.03) | (0.04) | | (0.05) | (0.01) | |
| AVE | D477A | 0.08 | 0.09 | 1.06 | 0.03 | 0.11 | 4.20 |
| SD | | (0.00) | (0.01) | | (0.04) | (0.02) | |

Fg = Fibrinogen
Fb = Fibrin
Pl = Plasma
PC = Plasma clot
AVE = Average
SD = Standard deviation

TABLE VI activities are relative to wt rt-PA (where wt is 1.0).
FIBRIN AND PLASMA CLOT SPECIFICITY OF rt-PA VARIANTS (TWO-CHAIN)

| | Mutant | Fg | Fb | Fb/Fg | Pl | PC | PC/Pl |
|---|---|---|---|---|---|---|---|
| AVE | R267A | 0.85 | 0.97 | 1.14 | 0.70 | 0.86 | 1.23 |
| SD | | (0.21) | (0.15) | | (0.08) | (0.11) | |
| AVE | D283A, | 0.77 | 1.00 | 1.31 | 0.68 | 0.82 | 1.19 |
| SD | H287A | (0.12) | (0.08) | | (0.14) | (0.04) | |
| AVE | K296A, | 0.31 | 2.82 | 9.24 | 0.24 | 1.29 | 5.50 |
| SD | H297A, R298A, R299A | (0.14) | (0.32) | | (0.15) | (0.20) | |
| AVE | E303A, | 0.56 | 2.13 | 3.79 | 0.26 | 1.34 | 5.10 |
| SD | R304A | (0.23) | (0.29) | | (0.08) | (0.10) | |
| AVE | H331A, | 1.03 | 2.19 | 2.12 | 1.03 | 1.61 | 1.56 |
| SD | H332A | (0.86) | (0.68) | | (0.67) | (0.68) | |
| AVE | R339A, | 0.55 | 1.04 | 1.89 | 0.23 | 0.79 | 3.38 |
| SD | R342A | (0.18) | (0.11) | | (0.05) | (0.10) | |
| AVE | E347A, | 0.76 | 1.33 | 1.76 | 0.44 | 0.97 | 2.20 |
| SD | E348A, E349A, K351A | (0.24) | (0.12) | | (0.11) | (0.10) | |
| AVE | D364A, | 0.73 | 1.77 | 2.44 | 0.26 | 1.46 | 5.68 |
| SD | D365A, D366A | (0.17) | (0.23) | | (0.12) | (0.15) | |
| AVE | K416A, | 0.77 | 0.96 | 1.24 | 0.42 | 0.77 | 1.82 |
| SD | H417A, E418A | (0.13) | (0.09) | | (0.08) | (0.05) | |
| AVE | E426A, | 0.38 | 0.76 | 2.01 | 0.24 | 0.66 | 2.80 |
| SD | R427A, K429A, E430A | (0.27) | (0.07) | | (0.07) | (0.12) | |
| AVE | H432A, | 0.16 | 0.99 | 6.40 | 0.16 | 0.38 | 2.31 |
| SD | R434A | (0.05) | (0.13) | | (0.05) | (0.05) | |
| AVE | R440A | 0.51 | 0.92 | 1.81 | 0.51 | 0.90 | 1.78 |
| SD | | (0.11) | (0.10) | | (0.08) | (0.09) | |
| AVE | H445A, | 0.62 | 1.46 | 2.36 | 0.29 | 1.19 | 4.06 |
| SD | R449A | (0.16) | (0.10) | | (0.09) | (0.11) | |
| AVE | R449A, | 0.74 | 1.50 | 2.04 | 0.36 | 1.22 | 3.36 |
| SD | D453A | (0.14) | (0.23) | | (0.12) | (0.13) | |
| AVE | D460A, | 0.18 | 1.04 | 5.91 | 0.12 | 0.32 | 2.59 |
| SD | R462A | (0.12) | (0.08) | | (0.02) | (0.02) | |
| AVE | D477A | 0.12 | 0.10 | 0.89 | 0.11 | 0.25 | 2.24 |
| SD | | (0.07) | (0.02) | | (0.03) | (0.08) | |

Fg = Fibrinogen
Fb = Fibrin
Pl = Plasma
PC = Plasma clot
AVE = Average
SD = Standard deviation

TABLE VII

| | Fibrin Specificity | | Plasma Clot Specificity | |
|---|---|---|---|---|
| Mutant | 1-chain | 2-chain | 1-chain | 2-chain |
| R267A | X | | X | |
| D283A,H287A | | | X | |
| K296A,H297A,R298A,R299A | X | X | X | X |
| E303A,R304A | X | X | X | X |
| H331A,H332A | | X | | X |

TABLE VII-continued

| Mutant | Fibrin Specificity | | Plasma Clot Specificity | |
|---|---|---|---|---|
| | 1-chain | 2-chain | 1-chain | 2-chain |
| R339A,R342A | | X | X | X |
| E347A,E348A,E349A,K351A | X | X | X | X |
| D364A,D365A,D366A | X | X | X | X |
| K416A,H417A,E418A | | | X | X |
| E426A,R427A,K429A,E430A | | X | X | X |
| H432A,R434A | | X | | X |
| R440A | X | X | X | X |
| H445A,R449A | X | X | X | X |
| R449A,D453A | X | X | X | X |
| D460A,R462A | X | X | X | X |
| D477A | | | X | X |

There was a striking correlation between those variants of rt-PA exhibiting fibrin and/or plasma clot specificity and those that meet the criteria of zymogenicity specified above. In addition, two variants of rt-PA were found to exhibit fibrin specificity but were not zymogenic relative to wild-type rt-PA. Table VIII shows the S-2251 assay data for the fibrin-specific and plasma clot-specific variants.

TABLE VIII

FIBRIN- AND PLASMA CLOT-SPECIFIC, NON-ZYMOGENIC VARIANTS OF rt-PA

| | Mutant | Fg/1ch | Fb/1ch | Fb/Fg1ch | Pl/1ch | PC/1ch | PC/Pl1ch |
|---|---|---|---|---|---|---|---|
| AVE | E408A | 0.35 | 0.79 | 2.28 | 0.19 | 0.47 | 2.51 |
| SD | | (0.01) | (0.06) | | (0.04) | (0.01) | |
| AVE | E410A | 0.61 | 0.90 | 1.47 | 0.51 | 0.74 | 1.44 |
| SD | | (0.08) | (0.04) | | (0.11) | (0.05) | |

| | Mutant | Fg/2ch | Fb/2ch | Fb/Fg2ch | Pl/2ch | PC/2ch | PC/Pl2ch |
|---|---|---|---|---|---|---|---|
| AVE | E408A | 0.34 | 0.89 | 2.61 | 0.24 | 0.64 | 2.72 |
| SD | | (0.18) | (0.11) | | (0.08) | (0.04) | |
| AVE | E410A | 0.55 | 0.92 | 1.67 | 0.48 | 0.88 | 1.84 |
| SD | | (0.13) | (0.09) | | (0.10) | (0.08) | |

Fg = Fibrinogen
Fb = Fibrin
Pl = Plasma
PC = Plasma clot
1ch = 1 chain
2ch = 2 chain
AVE = Average
SD = Standard deviation Deposit of Materials The following culture has been deposited with the American Type Culture Collection, 12301 Parklawn Drive, Rockville, Md., USA (ATCC):

| Strain | ATCC Dep. No. | Deposit Date |
|---|---|---|
| pTPA33-2 in *E. coli*MM294tonA | 68,059 | July 18, 1989 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organism will be made available by ATCC under the terms of the Budapest Treaty, and subject to an agreement between Genentech, Inc. and ATCC, which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of one aspect of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

What is claimed is:

1. A replicable expression vector containing and capable, in a transformant host cell, of expressing a DNA sequence encoding a t-PA variant having an amino acid substituted around amino acid position 305 of the amino acid sequence of wild-type human t-PA, wherein said variant has zymogenic character as compared to the corresponding wild-type t-PA.

2. A host cell transformed with the expression vector of claim 1.

3. The host cell of claim 2 which is prokaryotic cell.

4. The host cell of claim 2 which is eukaryotic cell.

* * * * *